(12) United States Patent
Nakatou et al.

(10) Patent No.: US 10,921,283 B2
(45) Date of Patent: Feb. 16, 2021

(54) GAS SENSOR FOR DETECTING CONCENTRATION OF SPECIFIC GAS COMPONENT

(71) Applicant: DENSO CORPORATION, Kariya (JP)

(72) Inventors: Mitsunobu Nakatou, Kariya (JP); Keigo Mizutani, Kariya (JP); Takashi Araki, Kariya (JP); Yuusuke Toudou, Kariya (JP)

(73) Assignee: DENSO CORPORATION, Kariya (JP)

( * ) Notice: Subject to any disclaimer, the term of this patent is extended or adjusted under 35 U.S.C. 154(b) by 717 days.

(21) Appl. No.: 15/105,177

(22) PCT Filed: Dec. 16, 2014

(86) PCT No.: PCT/JP2014/083289
§ 371 (c)(1),
(2) Date: Jun. 16, 2016

(87) PCT Pub. No.: WO2015/093488
PCT Pub. Date: Jun. 25, 2015

(65) Prior Publication Data
US 2016/0320334 A1   Nov. 3, 2016

(30) Foreign Application Priority Data

Dec. 16, 2013 (JP) ................... 2013-259417
Nov. 20, 2014 (JP) ................... 2014-235747

(51) Int. Cl.
*G01N 27/41* (2006.01)
*G01N 27/419* (2006.01)
(Continued)

(52) U.S. Cl.
CPC ......... *G01N 27/419* (2013.01); *G01N 27/409* (2013.01); *G01N 27/4067* (2013.01);
(Continued)

(58) Field of Classification Search
CPC .................................................. G01N 27/4067
See application file for complete search history.

(56) References Cited

U.S. PATENT DOCUMENTS 6,551,497 B1    4/2003  Gao et al.
2002/0104758 A1*  8/2002  Mizutani ............. G01N 27/419
                                                   204/427

FOREIGN PATENT DOCUMENTS

JP    2003-149199    *  5/2003  ........... G01N 27/416
JP    2003-166973       6/2003
(Continued)

*Primary Examiner* — Alexander S Noguerola
(74) *Attorney, Agent, or Firm* — Nixon & Vanderhye P.C.

(57) ABSTRACT

A gas sensor includes a solid electrolyte, a gas chamber, a reference gas chamber, a pump cell, a monitor cell, and a sensor cell. The gas chamber has a spatial width W0 constant in a width direction W orthogonal to the direction of flow of a gas in a position where the pump electrode, the monitor electrode, and the sensor electrode are provided on the solid electrolyte. An amount of shift ΔX1 of a central position O2 of a gap S in the width direction W between the monitor electrode and the sensor electrode from a central position O1 in the width direction of the pump electrode has relationship of ΔX1≤¼ W1 where the pump electrode has a width W1. In addition, positions ΔY1 of a of a side surface of the monitor electrode and of a side surface of the sensor electrode from the central position O1 in the width direction W of the pump electrode have relationship of ΔY1≤½ W1.

9 Claims, 16 Drawing Sheets

(51) Int. Cl.
    *G01N 33/00*     (2006.01)
    *G01N 27/407*     (2006.01)
    *G01N 27/406*     (2006.01)
    *G01N 27/409*     (2006.01)

(52) U.S. Cl.
    CPC ......... *G01N 27/4071* (2013.01); *G01N 27/41* (2013.01); *G01N 33/0036* (2013.01); *G01N 33/0037* (2013.01); *Y02A 50/20* (2018.01)

(56) References Cited

FOREIGN PATENT DOCUMENTS

| | | | | |
|---|---|---|---|---|
| JP | 2011-058834 | * | 3/2011 | ............. G01N 27/41 |
| JP | 2011-58834 | | 3/2011 | |
| JP | 2015-45581 | | 3/2015 | |
| JP | 2015-062013 | | 4/2015 | |
| WO | WO 2015/025924 | | 2/2015 | |

\* cited by examiner

GAS SENSOR FOR DETECTING CONCENTRATION OF SPECIFIC GAS COMPONENT

CROSS-REFERENCE TO RELATED APPLICATION

This application is the U.S. national phase of International Application No. PCT/JP2014/083289 filed Dec. 16, 2014, which designated the U.S. and claims the benefit of priority from earlier Japanese Patent Application Nos. 2013-259417 filed on Dec. 16, 2013, and 2014-235747 filed on Nov. 20, 2014 the entire contents of each of which are incorporated herein by reference.

TECHNICAL FIELD

The present disclosure relates to a gas sensor and specifically to a gas sensor for detecting concentration of a specific gas component in a gas.

BACKGROUND ART

A gas sensor for detecting concentration of a specific gas component is arranged in where an exhaust gas, such as an exhaust pipe of an engine, and detects concentration of nitrogen oxides (NOx), hydrocarbon (HC), and the like.

For example, in a gas sensor element disclosed in JP 2002-310987A, a solid electrolyte is provided with a pair of electrodes to form an oxygen pump cell, an oxygen monitor cell, and a sensor cell and detects concentration of a specific gas component in a gas introduced into its internal space. In addition, in the gas sensor element in Patent Literature above, in order to detect concentration of a specific gas component, without being affected by the oxygen concentration in the internal space, distances from a gas inlet to introduce a gas into the internal space to an electrode of the oxygen monitor cell and to an electrode of the sensor cell in end positions on the upstream side of flow of the gas are designed to be equivalent.

CITATION LIST

Patent Literature

PTL 1: JP 2002-310987A

However, in order to improve detection accuracy of concentration of a specific gas component by a gas sensor, only the configuration where positions of an electrode of an oxygen monitor cell and an electrode of the sensor cell are equivalent in a direction of gas flow in an internal space is insufficient. That is, when positions of arranging an electrode of an oxygen monitor cell and an electrode of a sensor cell shift relative to a position of arranging an electrode of an oxygen pump cell in a width direction orthogonal to a direction of gas flow in the internal space, the manner of contact by the gas to the electrode of the oxygen monitor cell is different from that to the electrode of the sensor cell. In this case, an amount of decomposing residual oxygen in the gas in the electrode of the oxygen monitor cell is different from that in the electrode of the sensor cell. It is thus not possible to improve the detection accuracy of concentration of a specific gas component by the gas sensor.

In addition, in a gas sensor provided with a heater, when positions of arranging an electrode of an oxygen monitor cell and an electrode of a sensor cell shift in a width direction relative to a heat generation portion in the heater, influence by electronic conduction to the electrode of the oxygen monitor cell is different from that to the electrode of the sensor cell. In this case as well, it is not possible to improve detection accuracy of concentration of a specific gas component by the gas sensor.

Hence it is desired to provide a gas sensor that is capable of improving detection accuracy of concentration of a specific gas component.

One aspect of the present disclosure is a gas sensor, measuring concentration of a specific gas component in a gas containing oxygen, including:

a plate shaped solid electrolyte having oxygen ion conductivity;

a gas chamber formed on a side of a first main surface of the solid electrolyte to have the gas introduced thereinto;

a reference gas chamber formed on a side of a second main surface of the solid electrolyte to have a reference gas introduced thereinto;

a pump electrode provided on the first main surface of the solid electrolyte;

a monitor electrode provided on the first main surface of the solid electrolyte and positioned on a downstream side in a direction of flow of the gas from a position where the pump electrode is provided;

a sensor electrode provided on the first main surface of the solid electrolyte and aligned in a direction perpendicular to the direction of the flow relative to a position where the monitor electrode is provided;

a reference electrode provided on the second main surface of the solid electrolyte; and a heater arranged facing the solid electrolyte via the gas chamber or the reference gas chamber to heat the solid electrolyte, wherein part of the pump electrode, the reference electrode, and the solid electrolyte forms a pump cell, the pump cell applying a voltage between the pump electrode and the reference electrode to adjust oxygen concentration in the gas in the gas chamber, part of the monitor electrode, the reference electrode, and the solid electrolyte forms a monitor cell to detect the oxygen concentration in the gas chamber on the basis of an oxygen ion current flowing between the monitor electrode and the reference electrode, part of the sensor electrode, the reference electrode, and the solid electrolyte forms a sensor cell to detect the oxygen concentration and the concentration of the specific gas component in the gas chamber on the basis of an oxygen ion current flowing between the sensor electrode and the reference electrode, the concentration of the specific gas component is detected by subtracting the oxygen ion current detected by the monitor cell from the oxygen ion current detected by the sensor cell, the gas chamber has a spatial width which is constant in a width direction orthogonal to the direction of flow in a position where the pump electrode, the monitor electrode, and the sensor electrode are provided on the solid electrolyte, and, in the width direction, an amount of shift $\Delta X1$ of a central position of a gap between the monitor electrode and the sensor electrode from a central position of the pump electrode has relationship of, where the pump electrode has a width $W1$, $\Delta X1 \leq \frac{1}{4} W1$, and positions $\Delta Y1$ of a side surface of the monitor electrode and of a side surface of the sensor electrode from the central position of the pump electrode have relationship of $\Delta Y1 \leq \frac{1}{2} W1$.

Another aspect of the present disclosure is a gas sensor, measuring concentration of a specific gas component in a gas containing oxygen, including:

a plate shaped solid electrolyte having oxygen ion conductivity;

a gas chamber formed on a side of a first main surface of the solid electrolyte to have the gas introduced thereinto;

a reference gas chamber formed on a side of a second main surface of the solid electrolyte to have a reference gas introduced thereinto;

a pump electrode provided on the first main surface of the solid electrolyte;

a monitor electrode provided on the first main surface of the solid electrolyte and positioned on a downstream side in a direction of flow of the gas from a position where the pump electrode is provided;

a sensor electrode provided on the first main surface of the solid electrolyte and aligned in a direction perpendicular to the direction of the flow relative to a position where the monitor electrode is provided;

a reference electrode provided on the second main surface of the solid electrolyte; and a heater arranged facing the solid electrolyte via the gas chamber or the reference gas chamber to heat the solid electrolyte, wherein part of the pump electrode, the reference electrode, and the solid electrolyte forms a pump cell, the pump cell applying a voltage between the pump electrode and the reference electrode to adjust oxygen concentration in the gas in the gas chamber, part of the monitor electrode, the reference electrode, and the solid electrolyte forms a monitor cell to detect the oxygen concentration in the gas chamber on the basis of an oxygen ion current flowing between the monitor electrode and the reference electrode, part of the sensor electrode, the reference electrode, and the solid electrolyte forms a sensor cell to detect the oxygen concentration and the concentration of the specific gas component in the gas chamber on the basis of an oxygen ion current flowing between the sensor electrode and the reference electrode, the concentration of the specific gas component is detected by subtracting the oxygen ion current detected by the monitor cell from the oxygen ion current detected by the sensor cell, the gas chamber has a spatial width which is constant in a width direction orthogonal to the direction of flow in a position where the pump electrode, the monitor electrode, and the sensor electrode are provided on the solid electrolyte, the heater has an insulator and a heat generation portion embedded in the insulator to generate heat by energization, the heat generation portion provided to correspond to a projected position of an entire plane region of the solid electrolyte provided with the pump electrode, the monitor electrode, and the sensor electrode, and, in the width direction, an amount of shift $\Delta X2$ of a central position of a gap between the monitor electrode and the sensor electrode from a central position of the heat generation portion has relationship of, where the heat generation portion has an entire width $W2$ in the width direction, $\Delta X2 \leq \frac{1}{4} W2$, and positions $\Delta Y2$ of a side surface of the monitor electrode and of a side surface of the sensor electrode from the central position of the heat generation portion satisfy a relationship of $\Delta Y2 \leq \frac{1}{2} W2$.

Still another aspect of the present disclosure is a gas sensor, measuring concentration of a specific gas component in a gas containing oxygen, including:

a plate shaped solid electrolyte having oxygen ion conductivity;

a gas chamber formed on a side of a first main surface of the solid electrolyte to have the gas introduced thereinto;

a reference gas chamber formed on a side of a second main surface of the solid electrolyte to have a reference gas introduced thereinto;

a pump electrode provided on the first main surface of the solid electrolyte;

a monitor electrode provided on the first main surface of the solid electrolyte and positioned on a downstream side in a direction of flow of the gas from a position where the pump electrode is provided;

a sensor electrode provided on the first main surface of the solid electrolyte and aligned in a direction perpendicular to the direction of the flow relative to a position where the monitor electrode is provided;

a reference electrode provided on the second main surface of the solid electrolyte; and a heater arranged facing the solid electrolyte via the gas chamber or the reference gas chamber to heat the solid electrolyte, wherein part of the pump electrode, the reference electrode, and the solid electrolyte forms a pump cell, the pump cell applying a voltage between the pump electrode and the reference electrode to adjust oxygen concentration in the gas in the gas chamber, part of the monitor electrode, the reference electrode, and the solid electrolyte forms a monitor cell to detect the oxygen concentration in the gas chamber on the basis of an oxygen ion current flowing between the monitor electrode and the reference electrode, part of the sensor electrode, the reference electrode, and the solid electrolyte forms a sensor cell to detect the concentration of the predetermined gas component in the gas chamber on the basis of an oxygen ion current flowing between the sensor electrode and the reference electrode, the concentration of the specific gas component is detected by subtracting the oxygen ion current detected by the monitor cell from the oxygen ion current detected by the sensor cell, the gas chamber is formed by a first gas chamber having the pump electrode arranged therein, a second gas chamber having the monitor electrode and the sensor electrode arranged therein, and a small space positioned between the first gas chamber and the second gas chamber, the small space has a narrower spatial width in a width direction in comparison with a spatial width in the width direction of the first gas chamber and a spatial width in the width direction of the second gas chamber, and, in the width direction, an amount of shift $\Delta X3$ of a central position of a gap between the monitor electrode and the sensor electrode from a central position of the small space has relationship of, where the small space has a spatial width $W3$ in the width direction, $\Delta X3 \leq \frac{1}{4} W3$.

Advantageous Effects of the Invention

In the gas sensor in the above one aspect, the pump electrode, the monitor electrode, the sensor electrode, and the reference electrode are provided on the same solid electrolyte. Then, the gas chamber has a spatial width constant in a position where the pump electrode, the monitor electrode, and the sensor electrode are provided on the solid electrolyte. In the structure of such gas sensor, definition of an amount of shift $\Delta X1$ of a central position in a width direction of a gap between the monitor electrode and the sensor electrode from a central position in the width direction of the pump electrode is important. Specifically, the amount of shift $\Delta X1$ has relationship of, where the pump electrode has a width of W1, $\Delta X1 \leq \frac{1}{4} W1$ (which means 0.25W1). The positions $\Delta Y1$ of respective side surfaces of the monitor electrode and the sensor electrode from the central position of the pump electrode satisfy a relationship of $\Delta Y1 \leq \frac{1}{2} W1$.

The tolerances for the amount of shift $\Delta X1$ and the positions $\Delta Y1$ of respective side surfaces from the central position are thus defined. Then, the gas after passing through the position where the pump electrode is arranged makes contact with the monitor electrode and the sensor electrode in a manner as equivalent as possible. Therefore, in the monitor electrode and the sensor electrode, the amounts of decomposing residual oxygen in the gas can be as equivalent as possible.

According to the gas sensor of this aspect, the detection accuracy of the concentration of a specific gas component is thus improved.

In the gas sensor in the above another aspect, the gas sensor has a basic structure the same as the gas sensor in the above one aspect. In the gas sensor in the above another aspect, tolerances for the amounts of shift in the width direction of the monitor electrode and the sensor electrode are defined in the relationship with the heat generation portion of the heater. Specifically, a tolerance for the amount of shift $\Delta X2$ of a central position in a width direction of a gap between the monitor electrode and the sensor electrode is defined relative to the central position in the width direction of the heat generation portion. Then, the amount of shift $\Delta X2$ has relationship of, where the heat generation portion has the entire width of W2 in the width direction, $\Delta X2 \leq \frac{1}{4} W2$ (which means 0.25W2). The positions $\Delta Y2$ of respective side surfaces of the monitor electrode and the sensor electrode from the central position of the heat generation portion have relationship of $\Delta Y2 \leq \frac{1}{2} W2$.

The tolerances for the amount of shift $\Delta X2$ and the positions $\Delta Y2$ of respective side surfaces from the central position are thus defined. The influence by electronic conduction from the heat generation portion, depending on the temperature of the solid electrolyte, thus occurs in the monitor electrode and the sensor electrode in a manner as equivalent as possible. When the monitor electrode and the sensor electrode are respectively affected by electronic conduction, a microcurrent flows through the monitor cell and the sensor cell, respectively. The microcurrents can cancel each other when the concentration of a specific gas component is obtained from the difference between the oxygen ion current in the sensor cell and the oxygen ion current in the monitor cell. Then, most of the influence of such microcurrents on detection of the concentration of a specific gas component can be eliminated.

Therefore, by the gas sensor in the above another aspect as well, the detection accuracy of the concentration of a specific gas component can be improved.

The configuration of the gas sensor in the above one aspect and the configuration of the gas sensor in the above another aspect can be applied at the same time in the same gas sensor.

In the gas sensor in the above still another aspect, when a small space is formed between the first gas chamber having the pump electrode arranged therein and the second gas chamber having the monitor electrode and the sensor electrode arranged therein, the amount of shift $\Delta X3$ of the central position in the width direction of the gap between the monitor electrode and the sensor electrode is defined relative to the central position in the width direction of the small space. Then, the amount of shift $\Delta X3$ has relationship of, where the small space has a spatial width W3 in the width direction, $\Delta X3 \leq \frac{1}{4} W3$.

The tolerance for the amount of shift $\Delta X3$ is thus defined. Then, the gas after passing through the small space from the position where the pump electrode is arranged makes contact with the monitor electrode and the sensor electrode in a manner as equivalent as possible. Therefore, in the monitor electrode and the sensor electrode, the amounts of decomposing residual oxygen in the gas can be as equivalent as possible.

Thus, by the gas sensor in the above still another aspect as well, the detection accuracy of the concentration of a specific gas component can be improved.

DETAILED DESCRIPTION OF THE PREFERRED EMBODIMENTS

Figure 1:
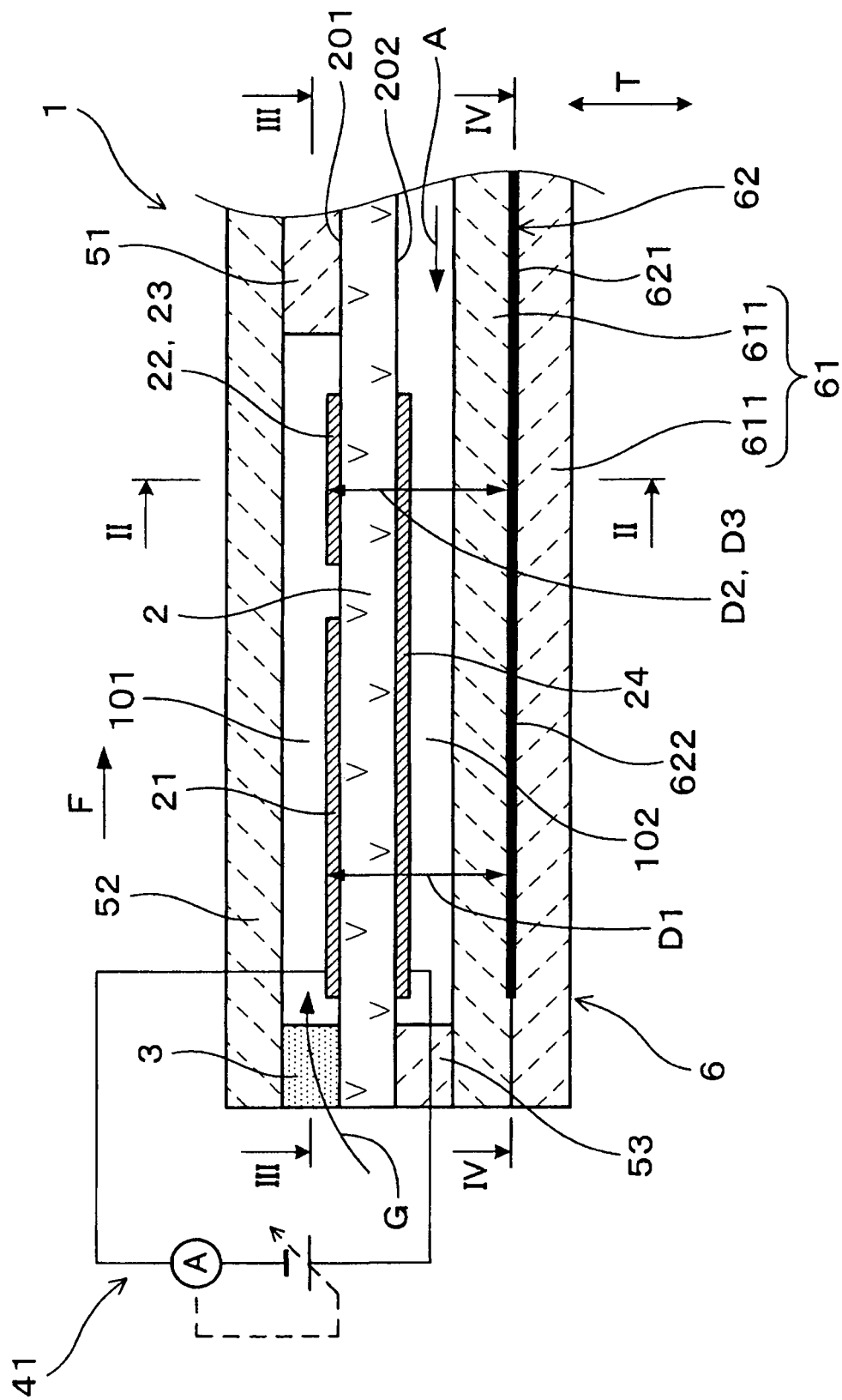
FIG. 1 is a cross-sectional view illustrating a gas sensor according to a first embodiment.

Preferred embodiments of the above gas sensor are described.

Although, the amount of shift ΔX1 and a position ΔY1 of each side surface from the central position in the gas sensor in the above one aspect, the amount of shift ΔX2 and the position ΔY2 of each side surface from the central position in the gas sensor in the above another aspect, and the amount of shift ΔX3 in the gas sensor in the above still another aspect are ideally 0 (zero), it is difficult to make them 0 in manufacture of a gas sensor. For this reason, the definition of the tolerance (ΔX1≤¼ W1) for the amount of shift ΔX1, the tolerance (ΔX2≤¼ W2) for the amount of shift ΔX2, and the tolerance (ΔX3≤¼ W3) for the amount of shift ΔX3 is significant.

The gas sensor in the above another aspect and the gas sensor in the above still another aspect can have, as shown in the gas sensor in the above one aspect, the relationship (ΔX1≤¼ W1) of the amount of shift ΔX1 and the relationship (ΔY1≤½ W1) of the position ΔY1 of each side surface from the central position.

The gas sensor in the above still another aspect can have, as shown in the gas sensor in the above another aspect, the relationship (ΔX2≤¼ W2) of the amount of shift ΔX2, and the relationship (ΔY2≤½ W2) of the position ΔY2 of each side surface from the central position.

In the gas sensor in the above one aspect, when two or more pump electrodes in the first main surface of the solid electrolyte are provided in alignment in the direction of gas flow, W1 used for the relationship of ΔX1≤¼ W1 can be the width of the pump electrode positioned on the most downstream side in the direction of gas flow. In this case, the central position in the width direction of the pump electrode used for the relationship of ΔY1≤½ W1 can be the central position of the pump electrode positioned on the most downstream side in the direction of gas flow.

In the gas sensor in the above one aspect, when a pump control electrode as another pump electrode used to control the pump cell is provided on the downstream side in the direction of gas flow of the pump electrode on the first main surface of the solid electrolyte, W1 used for the relationship of ΔX1≤¼W1 can be the width of the pump control electrode. In this case, the central position in the width direction of the pump electrode used for the relationship of ΔY1≤½ W1 can be the central position of the pump control electrode.

In the gas sensors in the above one aspect and the above another aspect, it is preferred that, in a thickness direction orthogonal to the width direction, a distance from a surface of the pump electrode to a surface of the heat generation portion, a distance from a surface of the monitor electrode to a surface of the heat generation portion, and a distance from a surface of the sensor electrode to a surface of the heat generation portion are approximately identical.

In this case, the influence by electronic conduction from the heat generation portion of the heater to the pump electrode, the monitor electrode, and the sensor electrode can be as equivalent as possible. Therefore, the temperatures of the pump electrode, the monitor electrode, and the sensor electrode can be readily controlled to optimum temperatures and the detection accuracy of the concentration of a specific gas component by the gas sensor can be improved.

By laminating the plate shaped solid electrolyte with the plate shaped heater and a heating portion, each of the above distances can be readily made same.

In addition, it is preferred that, in the width direction, a width of the monitor electrode and a width of the sensor electrode are approximately identical, and, in the direction of flow, a distance from an end face on a downstream side of the pump electrode to an end face on an upstream side of the monitor electrode and a distance from an end face on a downstream side of the pump electrode to an end face on an upstream side of the sensor electrode are approximately identical.

In this case, the gas after passing through the position where the pump electrode is arranged can make contact with the electrode of the monitor cell and the electrode of the sensor cell in a manner as equivalent as possible.

In the gas sensors in the above one aspect, the above another aspect, and the above still another aspect, it is preferred that the width W1 of the pump electrode and the entire width W2 of the heat generation portion have relationship of W1≤W2.

In this case, variation of temperature in temperature distribution in the width direction of the gas sensor can be minimized and the difference of the influence of the electronic conduction by the heat generation portion to the monitor electrode and to the sensor electrode can be reduced.

EMBODIMENTS

First Embodiment

An embodiment according to a gas sensor is described below with reference to the drawings.

Figure 2:
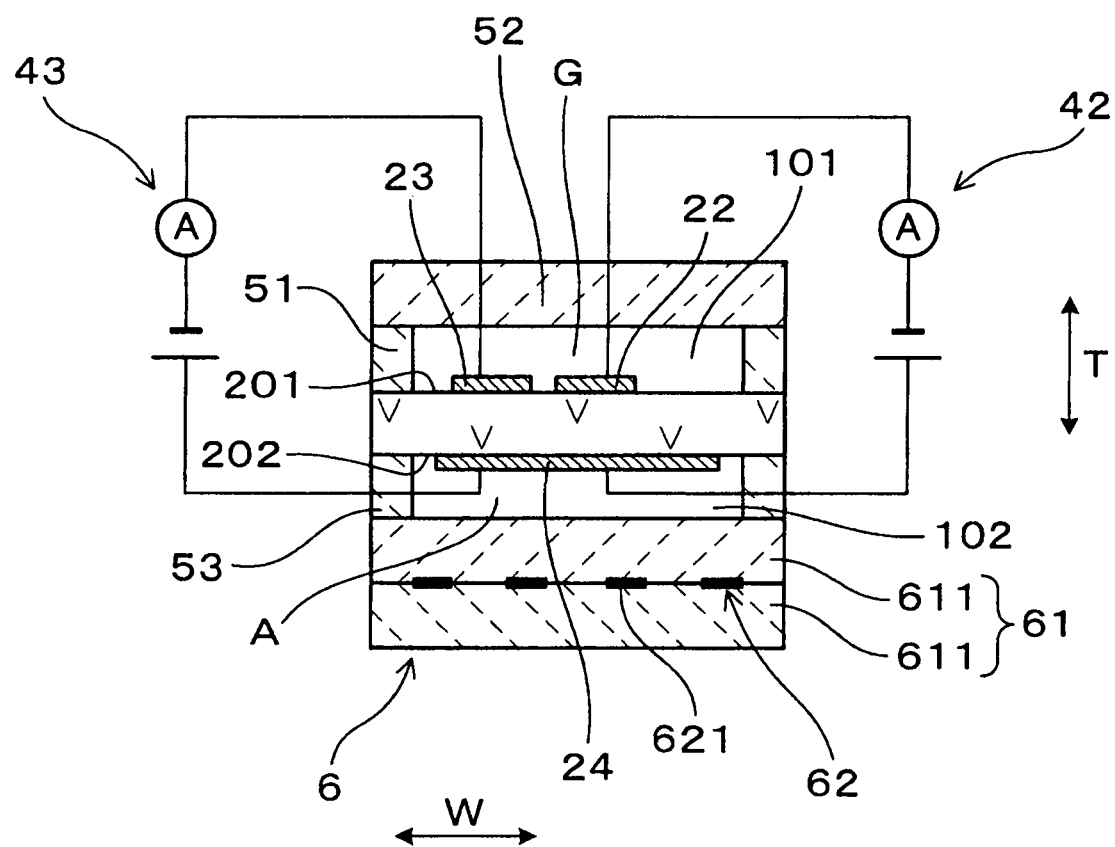
FIG. 2 is a II-II cross-sectional view of FIG. 1 according to the first embodiment.

A gas sensor 1 in the first embodiment is to measure concentration of a predetermined gas component in a gas G containing oxygen. As illustrated in FIGS. 1 and 2, the gas sensor 1 is provided with a solid electrolyte 2, a diffusion resistance 3, a gas chamber 101, a reference gas chamber 102, a pump cell 41, a monitor cell 42, a sensor cell 43, and a heater 6.

The solid electrolyte 2 has oxygen ion conductivity and is formed in a flat plate shape. The diffusion resistance 3 is formed from a porous material that reduces the flow rate of the gas G to let it to pass through in a predetermined amount of flow. The gas chamber 101 is formed on the side of a first main surface 201, which is one surface of the solid electrolyte 2, and formed as a space into which the gas G passing through the diffusion resistance 3 is introduced. The reference gas chamber 102 is formed on the side of a second main surface 202, which is the other surface of the solid electrolyte 2, and formed as a space into which a reference gas A is introduced. The second main surface 202 of the solid electrolyte 2 is provided with a reference electrode 24 to be exposed to the atmosphere as the reference gas A.

The pump cell 41 has a pump electrode 21 to be exposed to the gas G on the first main surface 201 of the solid electrolyte 2. The pump cell 41 is configured to apply a voltage between the pump electrode 21 and the reference electrode 24 to adjust oxygen concentration in the gas G in the gas chamber 101.

The monitor cell 42 has a monitor electrode 22 to be exposed to the gas G on the first main surface 201 of the solid electrolyte 2 and in a position on a downstream side from a position where the pump electrode 21 is arranged in a direction F of flow of the gas G. The monitor cell 42 is configured to detect the oxygen concentration in the gas G in the gas chamber 101 on the basis of an oxygen ion current flowing between the monitor electrode 22 and the reference electrode 24.

The sensor cell 43 has a sensor electrode 23 to be exposed to the gas G on the first main surface 201 of the solid electrolyte 2 and in a position aligned with a position where the monitor electrode 22 is arranged in a direction perpendicular to the direction F of flow of the gas G. The sensor cell 43 is used to detect the concentration of a specific gas component in the gas G in the gas chamber 101 on the basis of an oxygen Ion current flowing between the sensor electrode 23 and the reference electrode 24.

The heater 6 is to heat the solid electrolyte 2 and arranged facing the solid electrolyte (2) via the reference gas chamber 102.

Figure 3:
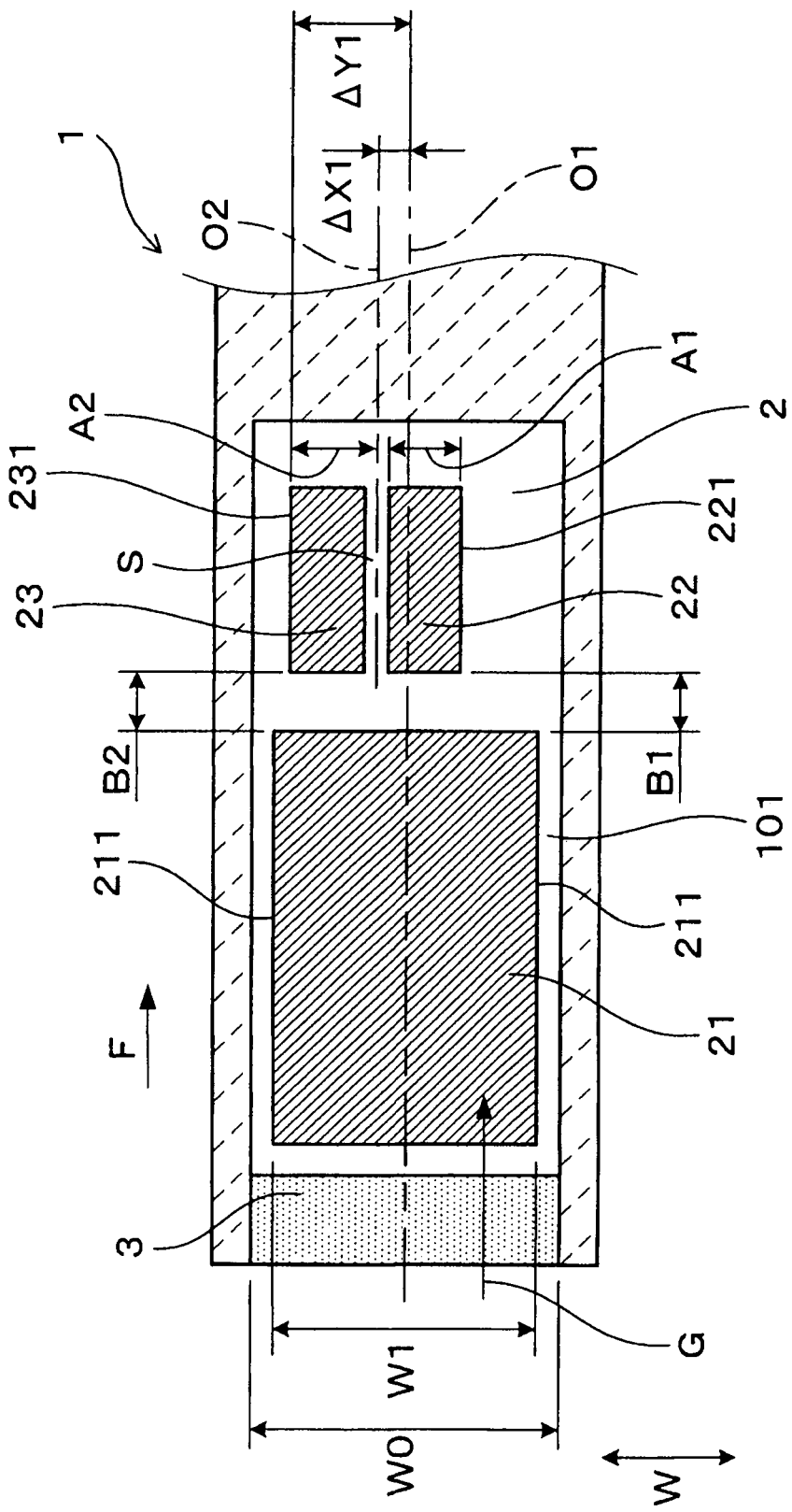
FIG. 3 is a III-III cross-sectional view of FIG. 1 according to the first embodiment.

As illustrated in FIGS. 2 and 3, the gas chamber 101 is formed surrounded by the solid electrolyte 2, insulators 51 and 52 laminated with the solid electrolyte 2, and the diffusion resistance 3. In the positions where the pump electrode 21, the monitor electrode 22, and the sensor electrode 23 are provided on the solid electrolyte 2, the gas chamber 101 has a spatial width W0 constant in a width direction W orthogonal to the direction F of flow of the gas G.

As illustrated in FIG. 3, where the pump electrode 21 has a width W1, an amount of shift $\Delta X1$ of a central position O2 in the width direction W of a gap S between the monitor electrode 22 and the sensor electrode 23 from a central position O1 in the width direction W of the pump electrode 21 has a relationship of $\Delta X1 \leq \frac{1}{4} W1$. Positions $\Delta Y1$ of a side surface 221 of the monitor electrode 22 and of a side surface 231 of the sensor electrode 23 from the central position O1 in the width direction W of the pump electrode 21 have a relationship of $\Delta Y1 \leq \frac{1}{2} W1$.

The gas sensor 1 in the first embodiment is described in detail below with reference to FIGS. 1 to 6.

The gas sensor 1 in the present embodiment is used in an exhaust pipe of an automobile in a state of being arranged in a cover. The gas G is an exhaust gas passing through the exhaust pipe, and the gas sensor 1 is used to detect concentration of NOx (nitrogen oxide) as a specific gas component in the exhaust gas.

The solid electrolyte 2 is a zirconia substrate having oxygen ion conductivity. The pump electrode 21, the monitor electrode 22, and the sensor electrode 23 are provided with a constant thickness on the first main surface 201 on the side to be exposed to the gas G. The reference electrode 24 is provided with a constant thickness on the second main surface 202 on the side to be exposed to the reference gas A in the solid electrolyte 2. The reference electrode 24 in the present embodiment is provided in a position on the back side in the entire region where the pump electrode 21, the monitor electrode 22, and the sensor electrode 23 are positioned in the solid electrolyte 2. Other than providing one reference electrode 24 relative to all of the pump electrode 21, the monitor electrode 22, and the sensor electrode 23, three reference electrodes 24 can be provided separately in the respective positions on the back side of the pump electrode 21, the monitor electrode 22, and the sensor electrode 23.

The reference electrode 24 is desirably formed, sandwiching the solid electrolyte 2, facing approximately the entire region where the pump electrode 21, the monitor electrode 22, and the sensor electrode 23 are formed on the first main surface 201 of the solid electrolyte 2. In other words, approximately all of the pump electrode 21, the monitor electrode 22, and the sensor electrode 23 are desirably included in a region where the reference electrode 24 is projected in a thickness direction T.

As illustrated in FIGS. 1 and 2, on the first main surface 201 on the gas G side of the solid electrolyte 2, the diffusion resistance 3 and a first insulator 51, which is a plate shaped substrate of alumina, are laminated. On surfaces of the diffusion resistance 3 and the first insulator 51, a second insulator 52, which is a plate shaped substrate of alumina, is laminated. The diffusion resistance 3 is arranged in an end portion on an upstream side in a longitudinal direction, which is the direction F of flow of the gas G in the gas sensor 1. The first insulator 51 is provided, on the first main surface 201 on the gas G side of the solid electrolyte 2, in an end portion on a downstream side in the longitudinal direction and in end portions on both sides in the width direction W to surround the pump electrode 21, the monitor electrode 22, and the sensor electrode 23 in three directions. The gas chamber 101 is formed, between the solid electrolyte 2 and the second insulator 52, surrounded by the diffusion resistance 3 and the first insulator 51 in four directions of the first main surface 201 on the gas G side of the solid electrolyte 2. In the positions where the pump electrode 21, the monitor electrode 22, and the sensor electrode 23 are provided on the solid electrolyte 2, the gas chamber 101 has a spatial height constant in the thickness direction T orthogonal to the direction F of flow and the width direction W.

As illustrated in FIGS. 1 and 2, on the second main surface 202 on the reference gas A side of the solid electrolyte 2, a third insulator 53, which is a plate shaped substrate of alumina, is laminated. The third insulator 53 is provided, on the second main surface 202 on the reference gas. A side of the solid electrolyte 2, in an end portion on an upstream side in a longitudinal direction and in end portions on both sides in the width direction W to surround the reference electrode 24 in three directions.

The heater 6 heats the solid electrolyte 2 and also heats the pump electrode 21, the monitor electrode 22, and the sensor electrode 23 provided on the solid electrolyte 2. The heater 6 is formed in a plate shape and laminated with the third insulator 53. The heater 6 has a fourth insulator 61 laminated on a surface of the third insulator 53 and an electrical conductor 62 provided in the fourth insulator 61 for energization. The fourth insulator 61 sandwiches the electrical conductor 62 with two insulating plates 611.

The reference gas chamber 102 is formed, between the solid electrolyte 2 and the fourth insulator 61, surrounded by the third insulator 53 in three directions of an end portion on an upstream side and end portions on both sides in the width direction W on the second main surface 202 on the reference gas A side of the solid electrolyte 2.

Figure 4:
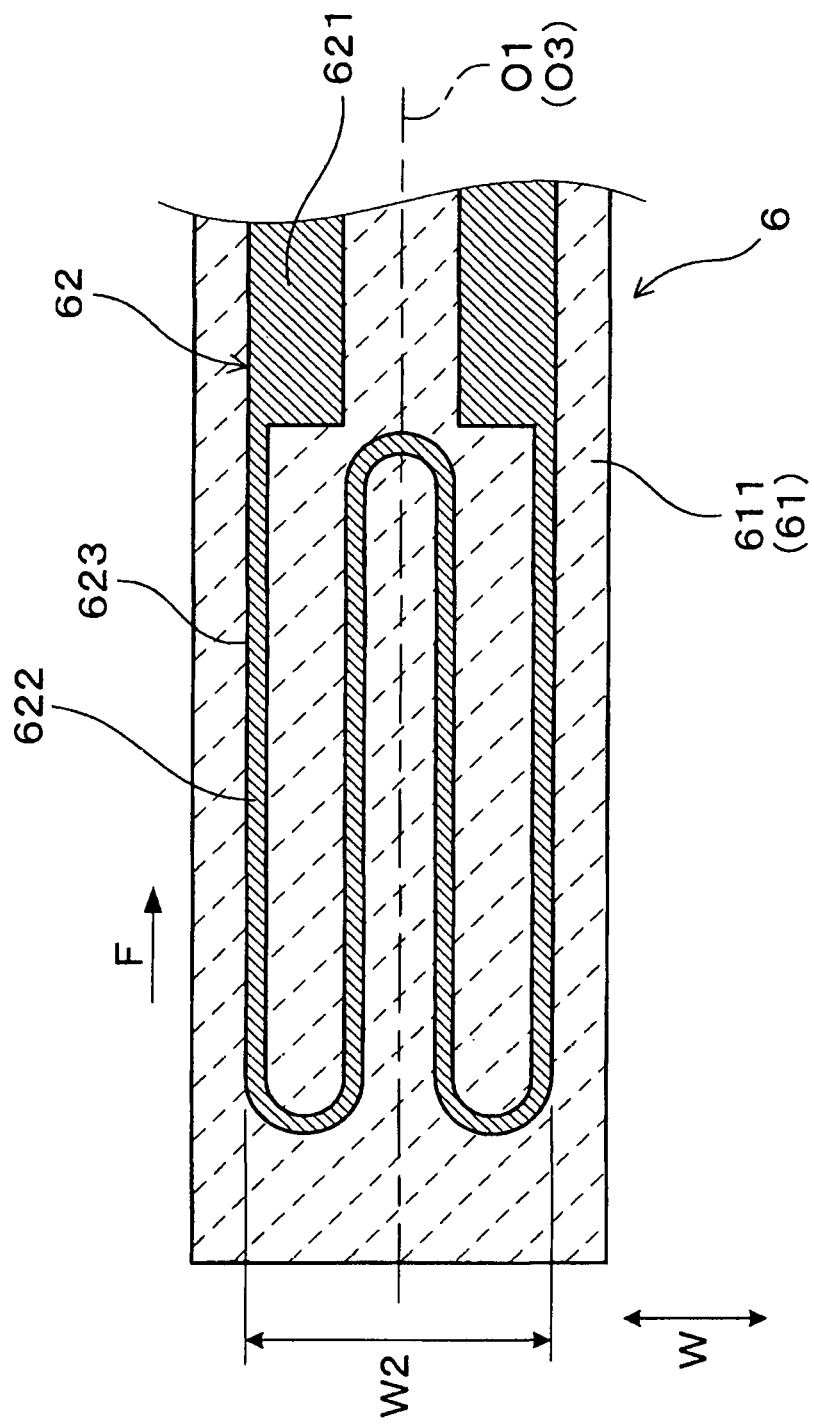
FIG. 4 is a IV-IV cross-sectional view of FIG. 1 according to the first embodiment.

As illustrated in FIG. 4, the electrical conductor 62 has a pair of electrode portions 621 connected to an external energization mechanism and a heat generation portion 622 linking the pair of electrode portions 621 to each other to generate heat by energization by a voltage applied to the pair of electrode portions 621.

The heat generation portion 622 has a cross-sectional area smaller than cross-sectional areas of the electrode portions 621. Then, the heat generation portion 622 has a resistance value per unit length greater than resistance values per unit length of the electrode portions 621. Therefore, when the pair of electrode portions 621 energizes the electrical conductor 62, heat is generated mainly in the heat generation portion 622 by Joule heat. Then, the heat generation in the heat generation portion 622 raises the temperature of the pump electrode 21, the monitor electrode 22, and the sensor electrode 23 to a desired activation temperature.

When the heat generation portion 622 has a film thickness the same as a film thickness of the electrode portions 621, the heat generation portion 622 has a pattern wire width which is formed in a width of, for example, approximately ¼ in comparison with a pattern wire width of the electrode portions 621. The resistance value of the heat generation portion 622 can be greater than the resistance values of the electrode portions 621 by making the film thickness of the heat generation portion 622 less than the film thickness of the electrode portions 621 or by making a specific resistance of a material constituting the heat generation portion 622 greater than a specific resistance of a material constituting the electrode portions 621. The resistance value of the heat generation portion 622 can also be greater than the resistance values of the electrode portions 621 by a combined method of differentiating the pattern wire width, the film thickness, the composition of the material, and the like.

The resistance value of the heat generation portion 622 occupies the proportion of 50% or more of the entire resistance value of the electrical conductor 62. The heat generation portion 622 is provided in a position where the entire plane region of the solid electrolyte 2 provided with the pump electrode 21, the monitor electrode 22, and the sensor electrode 23 is projected in the thickness direction T on a surface of the fourth insulator 61.

As illustrated in FIG. 1, the fourth insulator 61 and the electrical conductor 62 of the heater 6 are arranged in parallel with the solid electrolyte 2, and the electrical conductor 62 is arranged in parallel with the pump electrode 21, the monitor electrode 22, and the sensor electrode 23. Then, in the thickness direction T orthogonal to the direction F of flow and the width direction W in the gas sensor 1, a distance D1 from a surface of the pump electrode 21 to a surface of the heat generation portion 622, a distance D2 from a surface of the monitor electrode 22 to a surface of the heat generation portion 622, and a distance D3 from a surface of the sensor electrode 23 to a surface of the heat generation portion 622 are approximately equivalent. This enables each of the pump electrode 21, the monitor electrode 22, and the sensor electrode 23 to come close to the heat generation portion 622. The distance D1 from a surface of the pump electrode 21 to a surface of the heat generation portion 622, the distance D2 from a surface of the monitor electrode 22 to a surface of the heat generation portion 622, and the distance D3 from a surface of the sensor electrode 23 to a surface of the heat generation portion 622 may be slightly different, and more specifically, may be different up to ±10%.

A more oxygen ion current flows through the pump cell 41 including the pump electrode 21 in comparison with the monitor cell 42 including the monitor electrode 22 and the sensor cell 43 including the sensor electrode 23. Therefore, in order to facilitate heating of the pump electrode 21 slightly more in comparison with the monitor electrode 22 and the sensor electrode 23, a heat generating center of the heat generation portion 622 is arranged at an inclination to the pump electrode 21 side. The temperature of the pump electrode 21 is thus slightly higher in comparison with the temperature of the monitor electrode 22 and the temperature of the sensor electrode 23.

In this way, the heat generation portion 622 of the heater 6 readily controls the respective temperatures of the pump electrode 21, the monitor electrode 22, and the sensor electrode 23 to optimum temperatures.

In the width direction W of the gas sensor 1, the monitor electrode 22 has a width A1 approximately equivalent to a width A2 of the sensor electrode 23. The monitor electrode 22 in the present embodiment has an area approximately equivalent to an area of the sensor electrode 23. The width A1 of the monitor electrode 22 may be slightly different from the width A2 of the sensor electrode 23, and more specifically, may be different up to ±10%. The area of the monitor electrode 22 may be slightly different from the area of the sensor electrode 23, and more specifically, may be different up to ±10%.

The pump electrode 21 has an end face on the downstream side in parallel with the width direction W, and the monitor electrode 22 and the sensor electrode 23 have end faces on the upstream side in parallel with in the width direction W. Then, in the direction F of flow of the gas sensor 1, a distance B1 from the end face on the downstream side of the pump electrode 21 to the end face on the upstream side of the monitor electrode 22 and a distance B2 from the end face on the downstream side of the pump electrode 21 to the end face on the upstream side of the sensor electrode 23 are approximately equivalent. The distance B1 from the end face on the downstream side of the pump electrode 21 to the end face on the upstream side of the monitor electrode 22 may be slightly different from the distance B2 from the end face on the downstream side of the pump electrode 21 to the end face on the upstream side of the sensor electrode 23, and more specifically, may be different up to ±10%.

The monitor electrode 22 is an electrode not to decompose the specific gas component (NOx) in the gas G, and the sensor electrode is an electrode capable of decomposing the specific gas component in the gas G. In the monitor cell 42, an oxygen ion current is detected depending on the oxygen concentration, whereas in the sensor cell 43, an oxygen ion current is detected depending on the oxygen concentration and the NOx concentration. Then, in the gas sensor 1, by subtracting the oxygen ion current detected by the monitor cell 42 from the oxygen ion current detected by the sensor cell 43, the concentration of a specific gas component in the gas G is detected.

The gas sensor 1 in the present embodiment is provided with all of the pump electrode 21, the monitor electrode 22, the sensor electrode 23, and the reference electrode 24 on the same solid electrolyte 2 and has a specific structure in which the gas chamber 101 has the constant spatial width W0. Then in the gas sensor 1 of a specific structure, conditions of arranging the monitor electrode 22 and the sensor electrode 23 relative to the flow of the gas G after passing through the position where the pump electrode 21 is arranged in the gas chamber 101 are as equivalent as possible.

In such structure of the gas sensor 1, definition of the amount of shift $\Delta X1$ of the central position O2 in the width direction W of the gap S between the monitor electrode 22 and the sensor electrode 23 from the central position O1 in the width direction W of the pump electrode 21 is important. Specifically, where the pump electrode 21 has a width W1, the amount of shift $\Delta X1$ has relationship of $\Delta X1 \leq \frac{1}{4} W1$. The positions $\Delta Y1$ of the side surface 221 of the monitor electrode 22 and of the side surface 231 of the sensor electrode 23 relative to the central position O1 in the width direction W of the pump electrode 21 has relationship of $\Delta Y1 \leq \frac{1}{2} W1$. In other words, the position of the side surface 221 of the monitor electrode 22 is positioned the same as the position of the side surface 211 of the pump electrode 21 or inside from the position of the side surface 211 of the pump electrode 21. The position of the side surface 231 of the sensor electrode 23 is positioned same as the position of the side surface 211 of the pump electrode 21 or inside from the position of the side surface 211 of the pump electrode 21.

This enables definition of the tolerance for the amount of shift ΔX1 and the positions ΔY1 of the respective side surfaces 221 and 231 from the central position O1. Then, it allows the gas G after passing through the position where the pump electrode 21 is arranged to contact the monitor electrode 22 and the sensor electrode 23 in a manner as equivalent as possible. Therefore, the amounts of decomposing residual oxygen in the gas G can be as equivalent as possible in the monitor electrode 22 and the sensor electrode 23.

According to the gas sensor 1 in the first embodiment, the detection accuracy of the concentration of a specific gas component can be thus improved.

By making the distance B1 same as the distance B2, the amounts of decomposing residual oxygen in the gas G can be equivalent in the monitor electrode 22 and the sensor electrode 23. When both the distance B1 and the distance B2 are sufficiently long, the influence of the residual oxygen in the gas G on the monitor electrode 22 and the sensor electrode 23 becomes less. Note that, when both the distance B1 and the distance B2 are sufficiently long, the gas sensor 1 becomes longer in the longitudinal direction and other properties, such as responsiveness delay, are affected. The distance B1 and the distance B2 are therefore preferably determined within the range from 0.1 to 3.0 mm.

Figure 5:
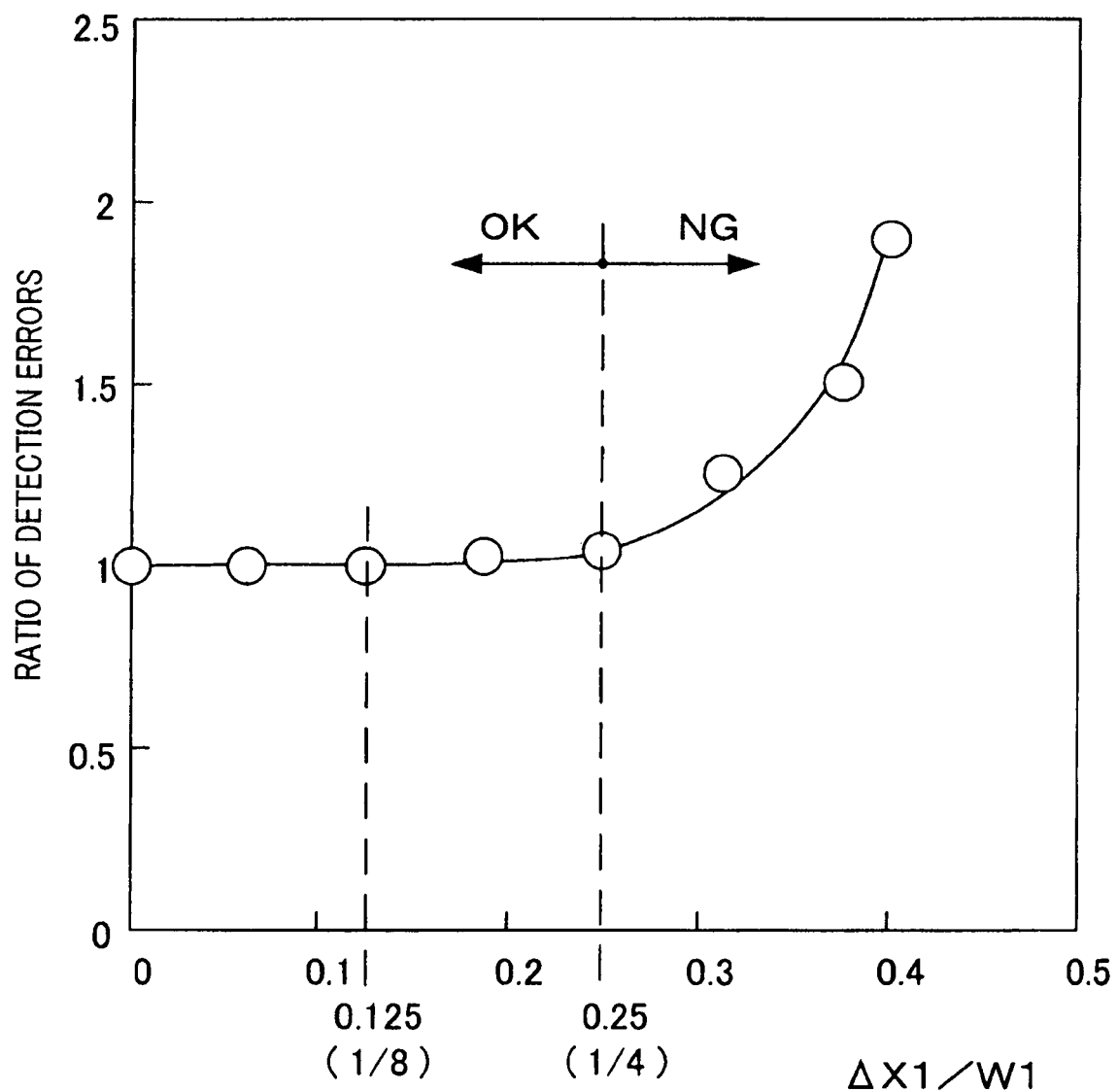
FIG. 5 is a graph, according to the first embodiment, illustrating a relationship between amount of shift $\Delta X1$ and a ratio of errors in detecting concentration of a specific gas component by the gas sensor.

FIG. 5 illustrates a relationship between the amount of shift ΔX1 and a ratio of errors in detecting concentration of a specific gas component by the gas sensor 1. FIG. 5 illustrates, where the detection error is defined as a reference value (one fold) for the amount of shift ΔX1 of 0 (zero), a ratio of increase (fold) of the detection errors relative to the reference value when the amount of shift ΔX1 varies. The illustration is for the case of the oxygen concentration in the gas G of 20%. As illustrated in FIG. 5, the detection errors gradually increase around from where the amount of shift ΔX1 is more than ⅛ W1 and the detection errors sharply increase around from where the amount of shift ΔX1 is more than ¼ W1.

For example, when the monitor electrode 22 is positioned on the central side in the width direction W and the sensor electrode 23 is positioned on the outer side in the width direction W, the residual oxygen in the gas G is considered to be decomposed more in the monitor electrode 22 in comparison with the sensor electrode 23. In this case, the amounts of oxygen ion current flowing through the monitor cell 42 and the sensor cell 43 are different due to the residual oxygen and the detection errors by the gas sensor 1 increase.

When the widths of the monitor electrode 22 and the sensor electrode 23 in the width direction W are as small as less than ¼ of the width of the pump electrode 21 in the width direction W, the amount of shift ΔX1 is allowed up to not more than ¼ W1 as long as the relationship of ΔY1≤½ W1 is satisfied. For this reason, the amount of shift ΔX1 preferably has relationship of ΔX1≤¼ W1 and even more preferably has relationship of ΔX1≤⅛ W1.

Figure 6:
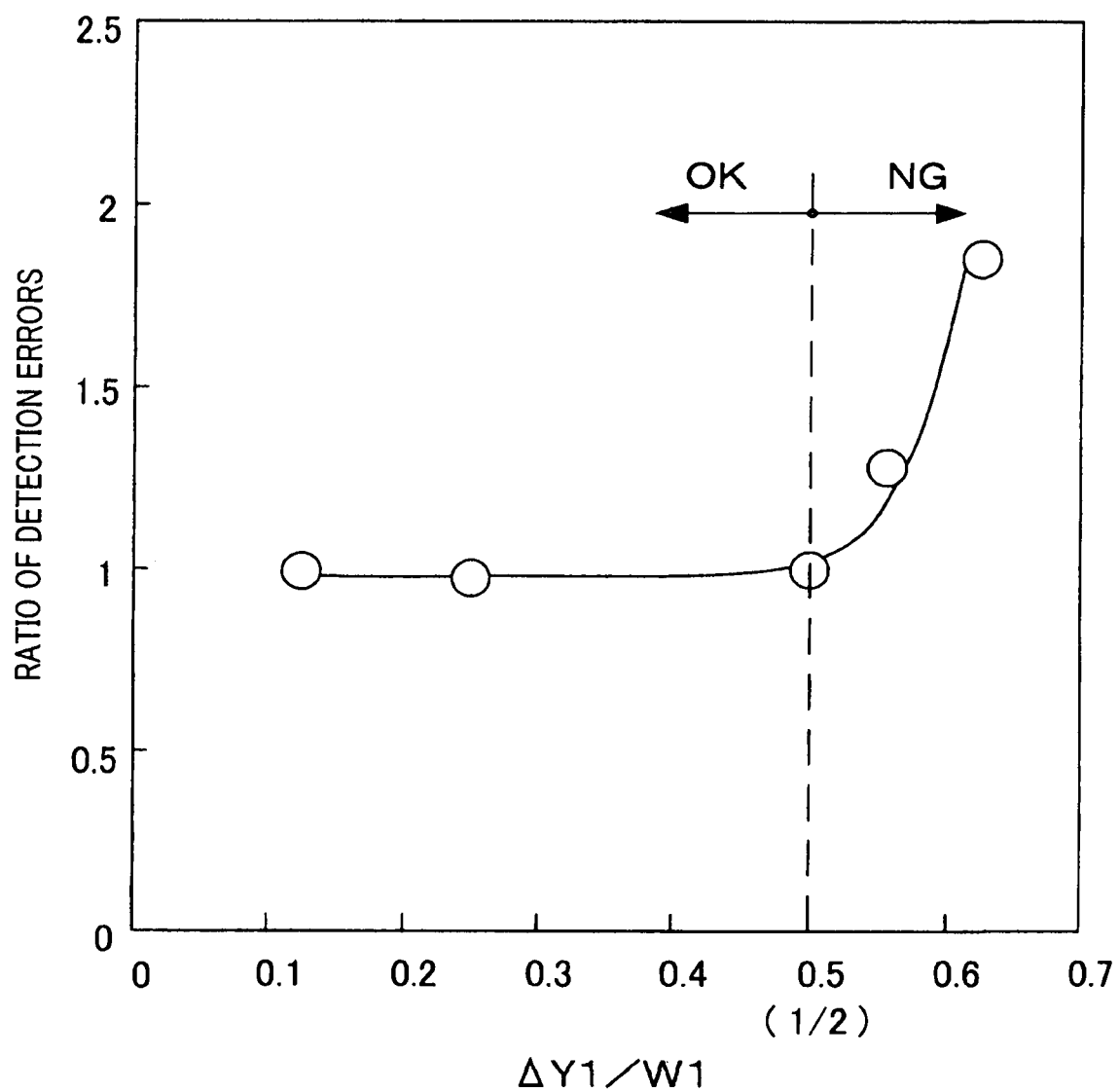
FIG. 6 is a graph, according to the first embodiment, illustrating a relationship between a position $\Delta Y1$ of a side surface of a monitor electrode or a sensor electrode from a central position in a width direction of a pump electrode and the ratio of errors in detecting concentration of a specific gas component by the gas sensor.

FIG. 6 illustrates relationship between the position ΔY1 of the side surface 221 or 231 of the monitor electrode 22 or the sensor electrode 23 from the central position O1 in the width direction W of the pump electrode 21 and the ratio of errors in detecting concentration of a specific gas component by the gas sensor 1. FIG. 6 illustrates, where the detection error is defined as a reference value (one fold) for the position of the side surface 221 of the monitor electrode 22 same as the position of the side surface 211 of the pump electrode 21, a ratio of increase (fold) of the detection errors relative to the reference value when the position ΔY1 of the side surface 221 or 231 varies. The illustration is for the case of the oxygen concentration in the gas G of 20%. As illustrated in FIG. 6, it is found that the detection errors increase around from where the position ΔY1 of the side surface 221 or 231 from the central position O1 is more than ½ W1. The reason for this is considered similarly to the case of the amount of shift ΔX1. For this reason, the position ΔY1 of the side surface 221 or 231 from the central position O1 preferably has relationship of ΔY1≤½ W1.

Second Embodiment

In the gas sensor 1 in the second embodiment, an amount of shift ΔX2 of the central position of the gap S between the monitor electrode 22 and the sensor electrode 23 is defined by the relationship of with the heat generation portion 622 in the heater 6.

Figure 7:
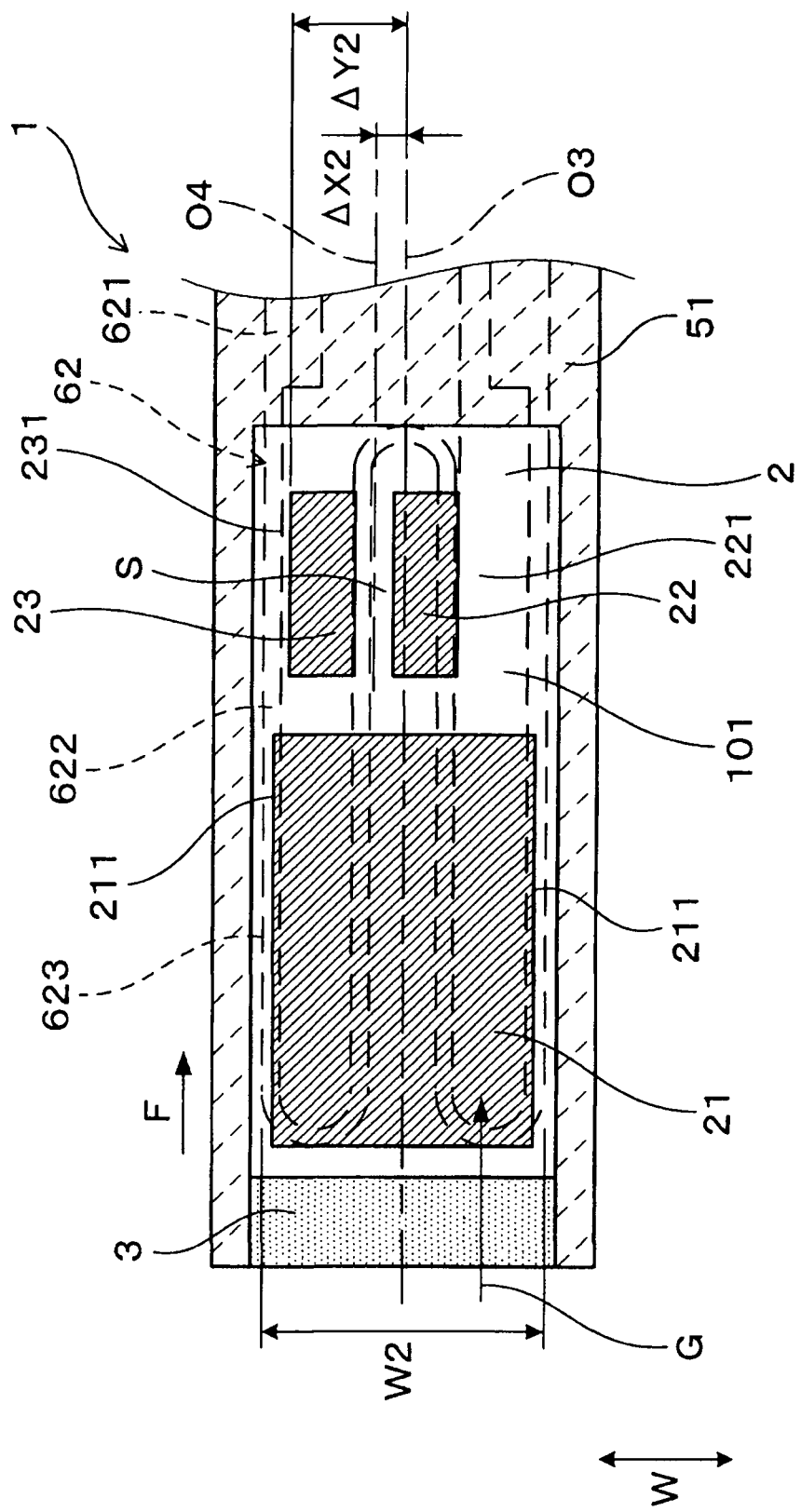
FIG. 7 is a diagram illustrating a gas sensor according to a second embodiment, which is a diagram equivalent to the III-III cross-section of FIG. 1.

Specifically, as illustrated in FIG. 7, in the width direction W of the gas sensor 1, an amount of shift ΔX2 of a central position O4 of the gap S between the monitor electrode 22 and the sensor electrode 23 from a central position O3 of the heat generation portion 622 has relationship of, where the heat generation portion 622 has the entire width W2 in the width direction W, ΔX2≤¼ W2.

In the width direction W of the gas sensor 1, positions ΔY2 of the side surface 221 of the monitor electrode 22 and of the side surface 231 of the sensor electrode 23 from the central position O3 of the heat generation portion 622 has relationship of ΔY2≤½ W2. In other words, the position of the side surface 221 of the monitor electrode 22 is positioned same as the position of the side surface 623 of the heat generation portion 622 or inside from the position of the side surface 623 of the heat generation portion 622. The position of the side surface 231 of the sensor electrode 23 is positioned same as the position of the side surface 623 of the heat generation portion 622 or inside from the position of the side surface 623 of the heat generation portion 622 (refer to FIG. 6).

Here, the heater 6 in the present embodiment has a structure same as that illustrated in FIG. 4 in the first embodiment. As illustrated in FIG. 4, both the central position O1 of the pump electrode 21 and the central position O3 of the heat generation portion 622 are in the central position of the gas sensor 1 in the width direction W.

The width W1 of the pump electrode 21 in the width direction W and the entire width W2 of the heat generation portion 622 in the width direction W have relationship of W1≤W2. This enables minimization of the variation of temperature in temperature distribution in the width direction W of the gas sensor 1 and reduction in the difference of influence of electronic conduction by the heat generation portion 622 on the monitor electrode 22 and the sensor electrode 23.

The gas sensor 1 in the present embodiment also has a specific structure similar to the case of the first embodiment. Then, in the gas sensor 1 of such specific structure, conditions of arranging the monitor electrode 22 and the sensor electrode 23 relative to the position of arranging the heat generation portion 622 of the heater 6 are as equivalent as possible. Specifically, in the gas sensor 1 of such specific structure, the amount of shift ΔX2 has relationship of ΔX2≤¼ W2, and the positions ΔY2 of the respective side surfaces 221 and 231 from the central position O3 have relationship of ΔY2≤½ W2.

This enables definition of the tolerance for the amount of shift ΔX2 and the positions ΔY2 of the respective side surfaces 221 and 231 from the central position O3. Then, it allows the electronic conduction from the heat generation portion 622 depending on the temperature of the solid electrolyte 2 to influence the monitor electrode 22 and the sensor electrode 23 in a manner as equivalent as possible. When the monitor electrode 22 and the sensor electrode are respectively influenced by the electronic conduction, a microcurrent flows respectively through the monitor cell 42 and the sensor cell 43. The microcurrents can cancel each other when the concentration of a specific gas component is obtained from the difference between the oxygen ion current in the sensor cell 43 and the oxygen ion current in the monitor cell 42. Then, most of the influence of such microcurrent on the detection of the concentration of a specific gas component can be eliminated.

According to the gas sensor 1 in the first embodiment, the detection accuracy of the concentration of a specific gas component can be thus improved.

In addition, the gas sensor 1 in the present embodiment also preferably has the relationship of $\Delta X1 \leq \frac{1}{4} W1$ and the relationship of $\Delta Y1 \leq \frac{1}{2} W1$ described in the first embodiment.

Other configurations and the reference signs in the drawings of the gas sensor 1 in the second embodiment are same as those in the first embodiment and other actions and effects of the second embodiment are same as those in the first embodiment.

Figure 8:
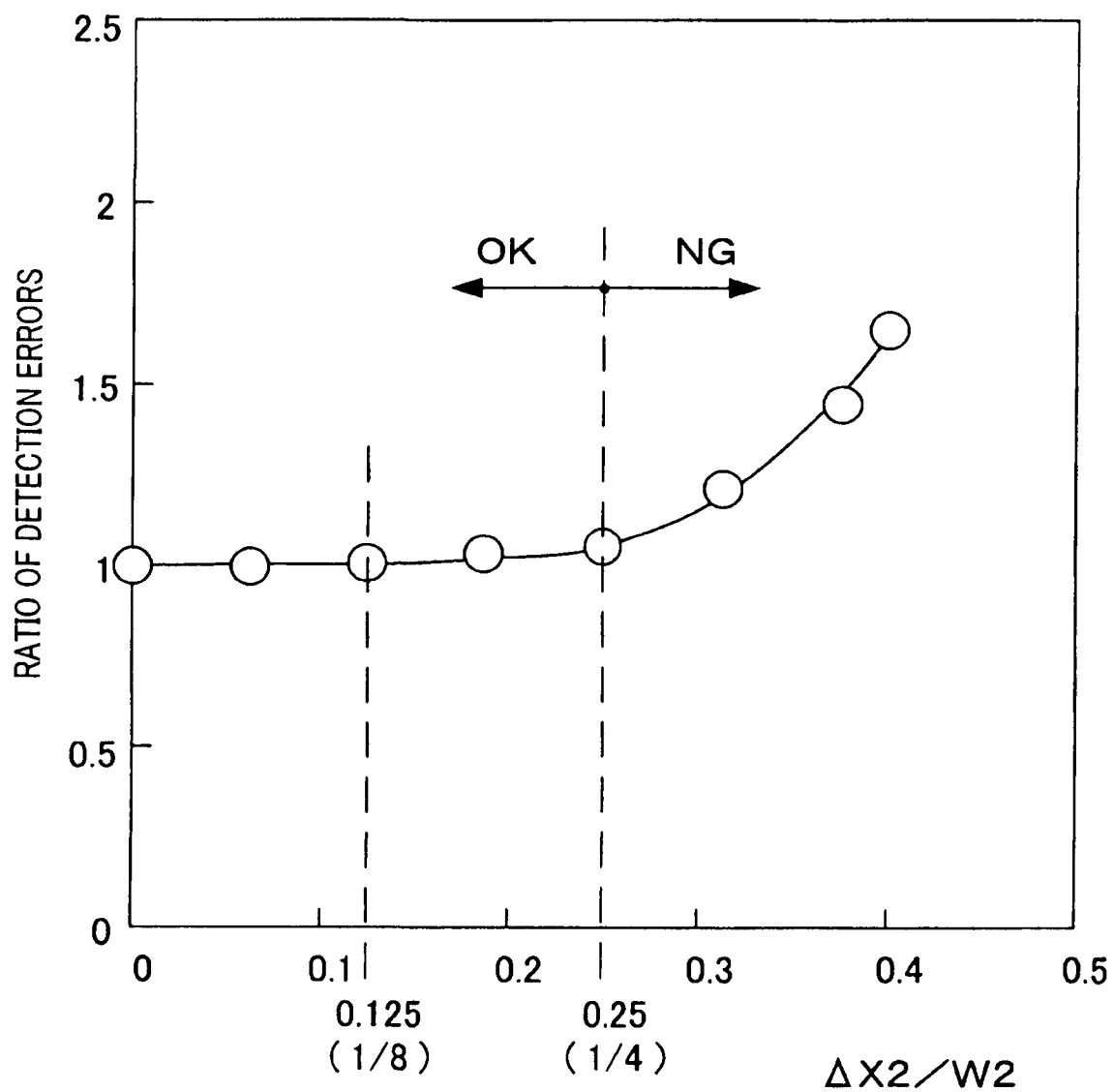
FIG. 8 is a graph, according to a second embodiment, illustrating relationship between an amount of shift $\Delta X2$ and a ratio of errors in detecting concentration of a specific gas component by the gas sensor.

FIG. 8 illustrates a relationship between the amount of shift $\Delta X2$ and the ratio of errors in detecting concentration of a specific gas component by the gas sensor 1. FIG. 8 illustrates, where the detection errors is defined as a reference value (one fold) for the amount of shift $\Delta X2$ of 0 (zero), a ratio of increase (fold) of the detection errors relative to the reference value when the amount of shift $\Delta X2$ varies. The illustration is for the case of the oxygen concentration in the gas G of 20%. As illustrated in FIG. 8, the detection errors gradually increase around from where the amount of shift $\Delta X2$ is more than $\frac{1}{8} W2$ and the detection errors sharply increase around from where the amount of shift $\Delta X2$ is more than $\frac{1}{4} W2$.

For example, when the monitor electrode 22 is positioned on the central side in the width direction W and the sensor electrode 23 is positioned on the outer side in the width direction W, the temperature is higher in the monitor electrode 22 in comparison with the sensor electrode 23 and the monitor electrode 22 is considered to be affected by the electronic conduction more in comparison with the sensor electrode 23. In this case, the influence of the microcurrent due to the electronic conduction on the oxygen ion current in the sensor cell 43 and on the oxygen ion current in the monitor cell 42 cannot cancel each other and the detection errors by the gas sensor 1 increase.

When the widths of the monitor electrode 22 and the sensor electrode 23 in the width direction W are as small as less than $\frac{1}{4}$ of the width of the heat generation portion 622 in the width direction W, the amount of shift $\Delta X2$ is allowed to be up to not more than $\frac{1}{4} W2$ as long as the relationship of $\Delta Y2 \leq \frac{1}{2} W2$ is satisfied. For this reason, the amount of shift $\Delta X2$ preferably has relationship of $\Delta X2 \leq \frac{1}{4} W2$ and even more preferably has relationship of $\Delta X2 \leq \frac{1}{8} W2$.

Figure 9:
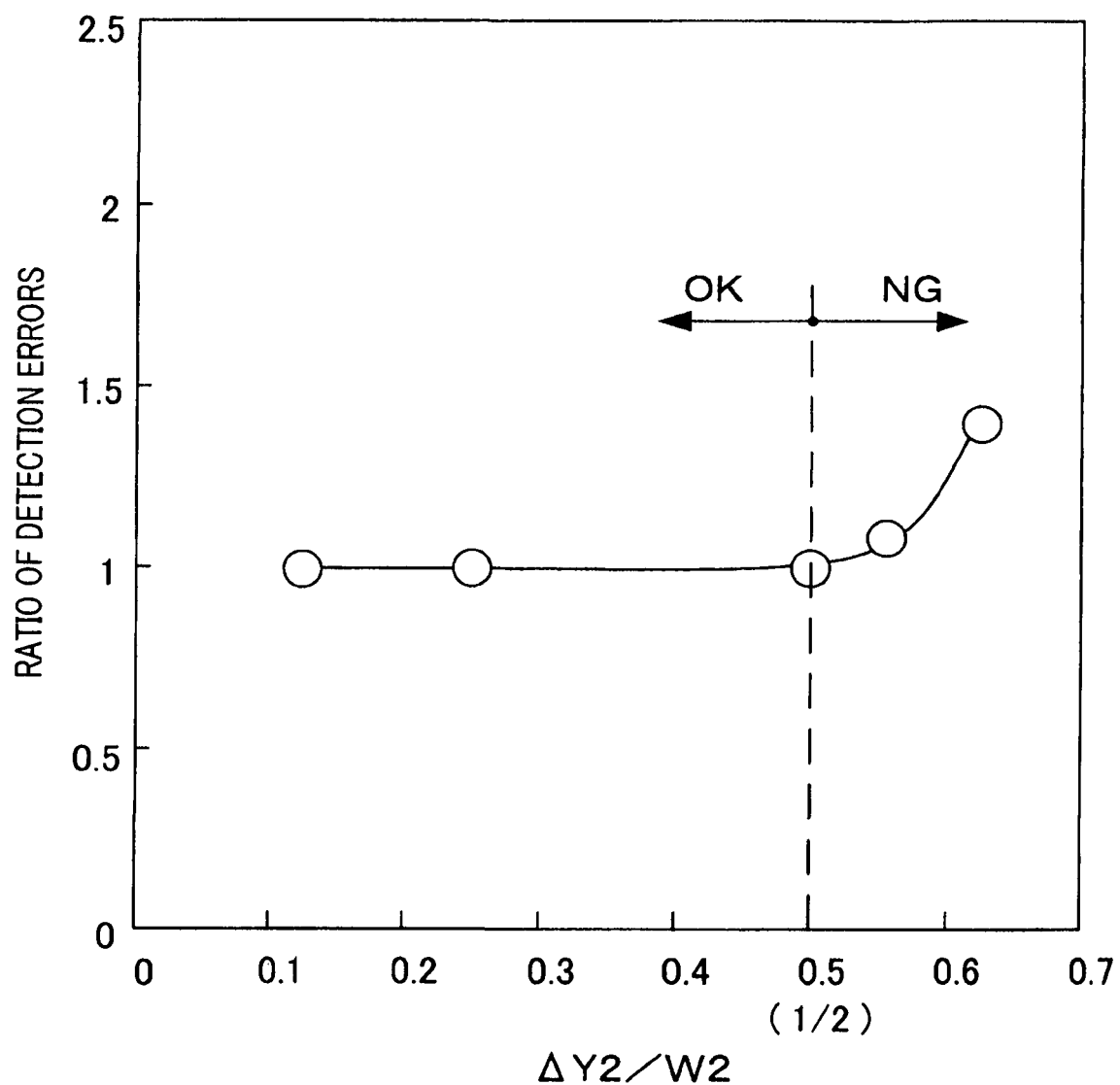
FIG. 9 is a graph, according to the second embodiment, illustrating a relationship between a position $\Delta Y2$ of a side surface of a monitor electrode or a sensor electrode from a central position in a width direction of a pump electrode and the ratio of errors in detecting concentration of a specific gas component by the gas sensor.

FIG. 9 illustrates a relationship between the position $\Delta Y2$ of the side surface 221 or 231 of the monitor electrode 22 or the sensor electrode 23 from the central position O3 in the width direction W of the heat generation portion 622 and the ratio of errors in detecting concentration of a specific gas component by the gas sensor 1. FIG. 9 illustrates, where the detection error is defined as a reference value (one fold) for the position of the side surface 221 of the monitor electrode 22 same as the position of the side surface 623 of the heat generation portion 622, a ratio of increase (fold) of the detection errors relative to the reference value when the position $\Delta Y2$ of the side surface 221 or 231 varies.

The illustration is for the case of the oxygen concentration in the gas G of 20%. As illustrated in FIG. 9, it is found that the detection errors increase around from where the position $\Delta Y2$ of the side surface 221 or 231 is more than $\frac{1}{2} W2$. The reason for this is considered similarly to the case of the amount of shift $\Delta X2$. For this reason, the position $\Delta Y2$ of the side surface 221 or 231 preferably has relationship of $\Delta Y2 \leq \frac{1}{2} W2$.

Figure 10:
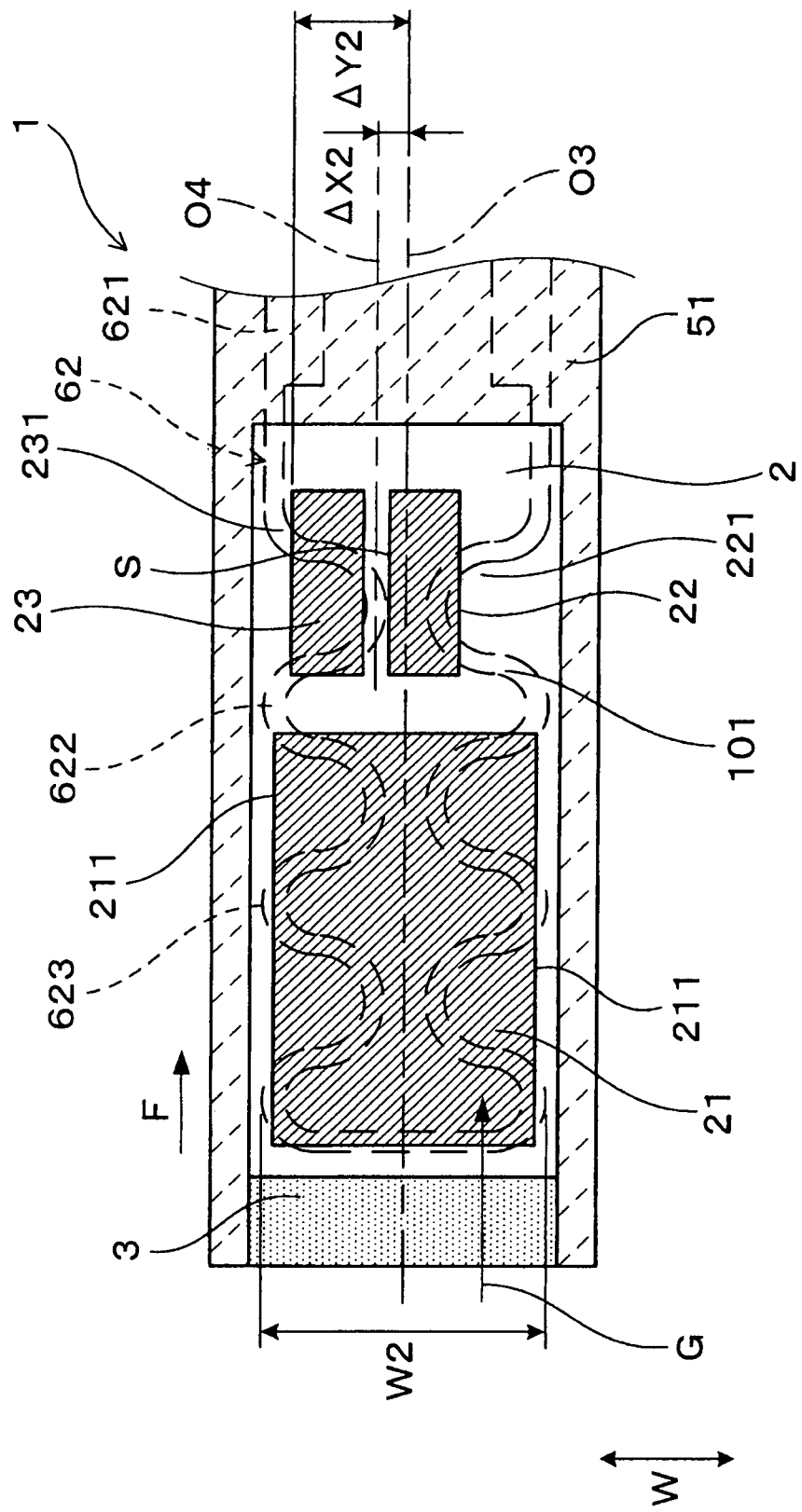
FIG. 10 is a diagram illustrating another gas sensor according to the second embodiment, which is a diagram equivalent to the III-III cross-section of FIG. 1.

The heat generation portion 622 may be formed approximately symmetrically in the width direction W of the gas sensor 1. The central position O3 of the heat generation portion 622 is equivalent to an axis of symmetry in the width direction W. The heat generation portion 622 can be formed in, for example, a pattern as illustrated in FIG. 10. In this case, the actions and effects are same as those in the second embodiment.

Third Embodiment

Figure 11:
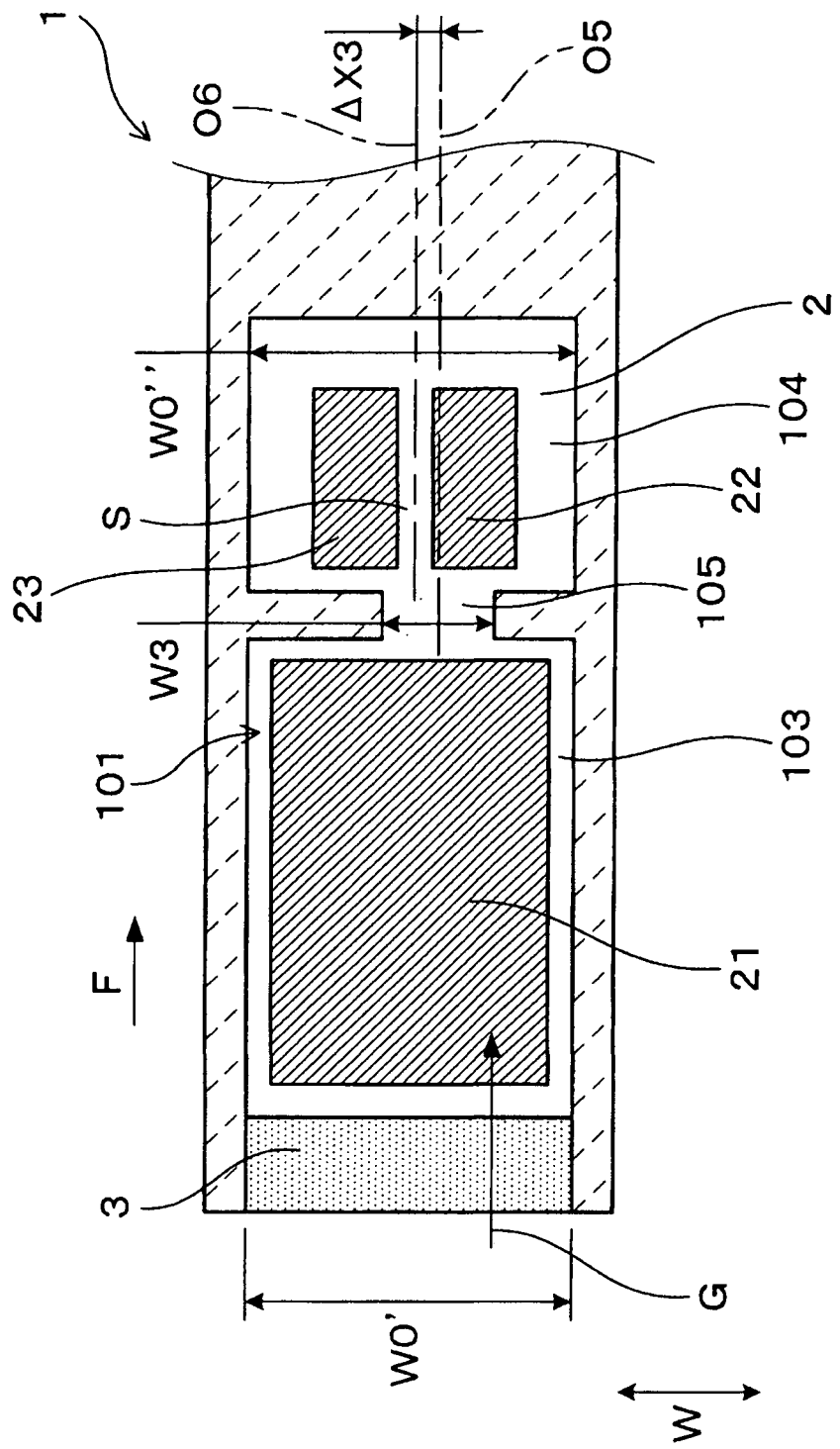
FIG. 11 is a diagram illustrating a gas sensor according to a third embodiment, which is a diagram equivalent to the III-III cross-section of FIG. 1.

As illustrated in FIG. 11, the third embodiment shows the case where the gas chamber 101 is formed by a first gas chamber 103 having the pump electrode 21 arranged therein, a second gas chamber 104 having the monitor electrode 22 and the sensor electrode 23 arranged therein, and a small space 105 positioned between the first gas chamber 103 and the second gas chamber 104.

The small space 105 has a spatial width W3 in the width direction W narrower in comparison with a spatial width W0' of the first gas chamber 103 in the width direction W and a spatial width W0" of the second gas chamber 104 in the width direction W. The spatial width W0' of the first gas chamber 103 and the spatial width W0" of the second gas chamber 104 are approximately same.

In the gas sensor 1 in the third embodiment, conditions of arranging the monitor electrode 22 and the sensor electrode 23 are as equivalent as possible relative to the flow of the gas G after passing through the small space 105 in the gas chamber 101. Then, in the width direction W of the gas sensor 1, an amount of shift $\Delta X3$ of a central position O6 of the gap S between the monitor electrode 22 and the sensor electrode 23 from a central position O5 of the small space 105 has relationship of $\Delta X3 \leq \frac{1}{4} W3$. This enables definition of the tolerance for the amount of shift $\Delta X3$. Then, it allows the gas G after passing through the small space 105 from the position where the pump electrode 21 is arranged to contact the monitor electrode 22 and the sensor electrode 23 in a manner as equivalent as possible. Therefore, the amounts of decomposing residual oxygen in the gas G can be as equivalent as possible in the monitor electrode 22 and the sensor electrode 23.

According to the gas sensor 1 in the first embodiment, the detection accuracy of the concentration of a specific gas component can be thus improved.

In addition, the gas sensor 1 in the present embodiment also preferably has the relationship of $\Delta X1 \leq \frac{1}{4} W1$ and the relationship of $\Delta Y1 \leq \frac{1}{2} W1$ described in the first embodiment. Moreover, it preferably has the relationship of $\Delta X2 \leq \frac{1}{4} W2$ and the relationship of $\Delta Y2 \leq \frac{1}{2} W2$ described in the second embodiment.

Other configurations and the reference signs in the drawings of the gas sensor 1 in the third embodiment are same as those in the first and second embodiments and other actions and effects of the present embodiment are same as those in the first and second embodiments.

Figure 12:
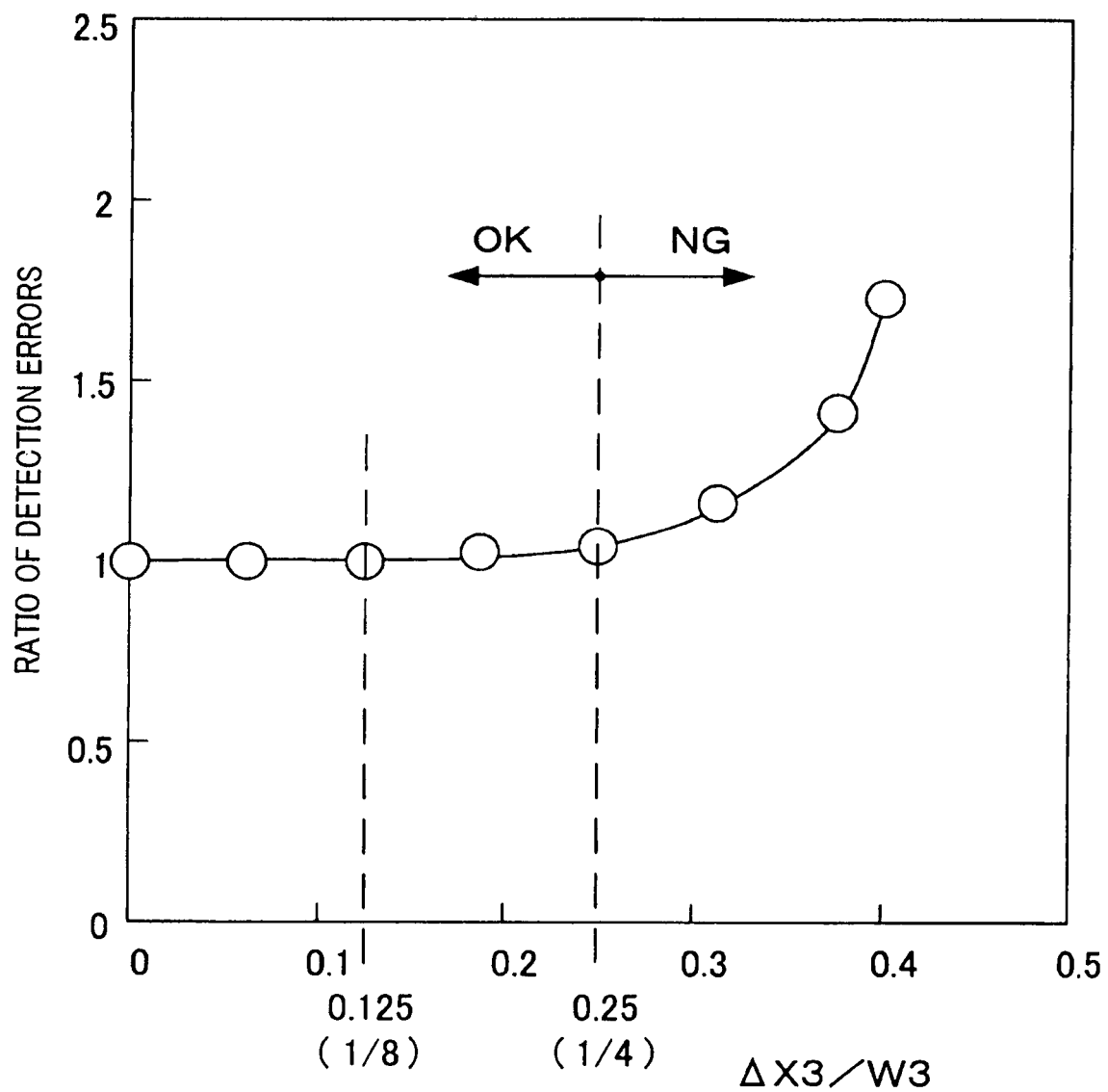
FIG. 12 is a graph, according to the third embodiment, illustrating a relationship between an amount of shift $\Delta X3$ and a ratio of errors in detecting concentration of a specific gas component by the gas sensor.

FIG. 12 illustrates relationship between the amount of shift ΔX3 and the ratio of errors in detecting concentration of a specific gas component by the gas sensor 1. FIG. 12 illustrates, where the detection errors is defined as a reference value (one fold) for the amount of shift ΔX2 of 0 (zero), a ratio of increase (fold) of the detection errors relative to the reference value when the amount of shift ΔX3 varies. The illustration is for the case of the oxygen concentration in the gas G of 20%. As illustrated in FIG. 12, the detection errors gradually increase around from where the amount of shift ΔX3 is more than ⅛ W3 and the detection errors sharply increase around from where the amount of shift ΔX3 is more than ¼ W3.

For example, when the monitor electrode 22 is positioned on the central side in the width direction W of the small space 105 and the sensor electrode 23 is positioned on the outer side in the width direction W, the residual oxygen in the gas G is considered to be decomposed more in the monitor electrode 22 in comparison with the sensor electrode 23. In this case, the amounts of oxygen ion current flowing through the monitor cell 42 and the sensor cell 43 are different due to the residual oxygen and the detection errors by the gas sensor 1 increase.

For this reason, the amount of shift ΔX3 preferably has relationship of ΔX3≤¼ W3 and even more preferably has relationship of ΔX3≤⅛ W3.

Fourth Embodiment

Figure 13:
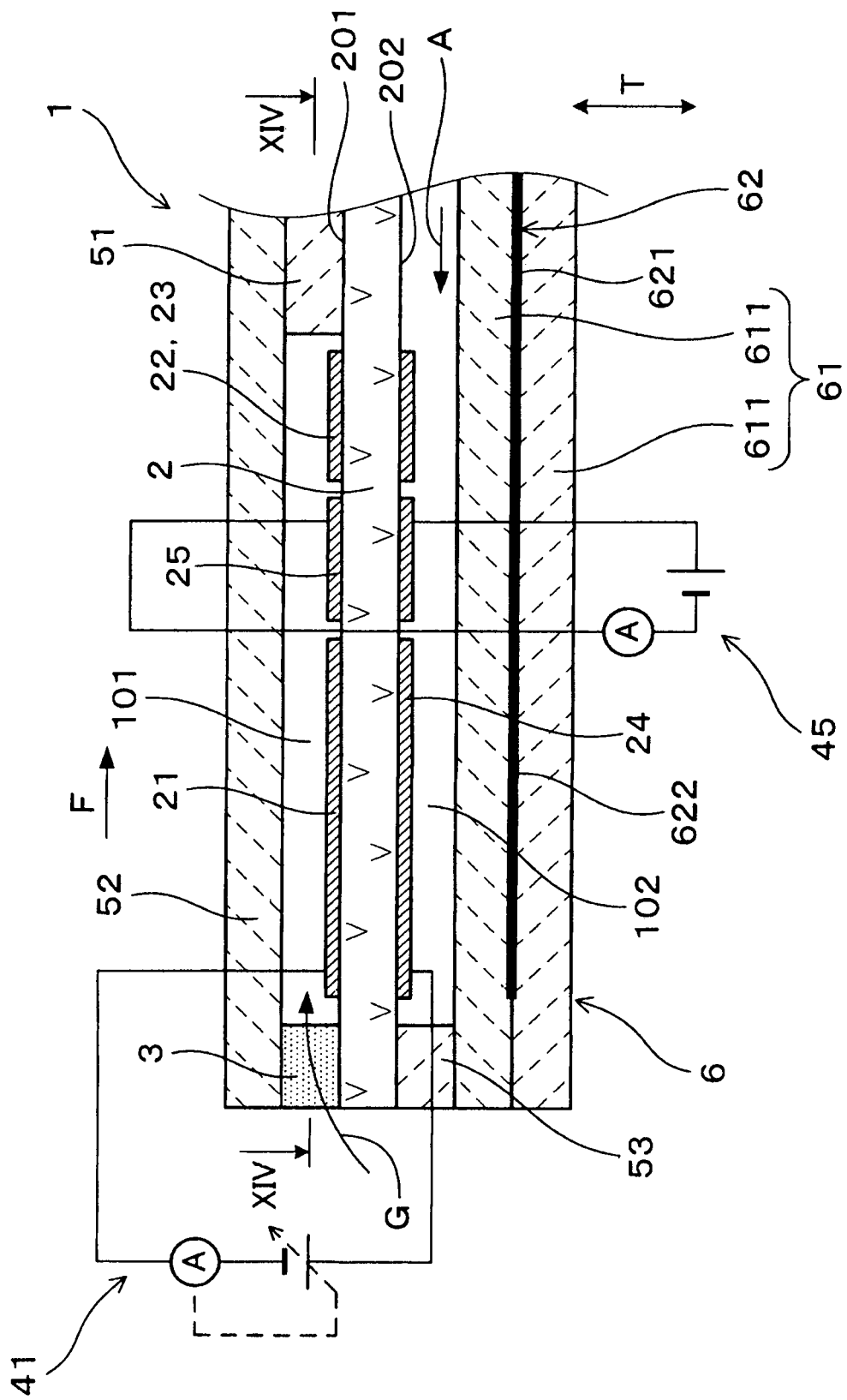
FIG. 13 is a cross-sectional view illustrating a gas sensor according to a fourth embodiment.
Figure 14:
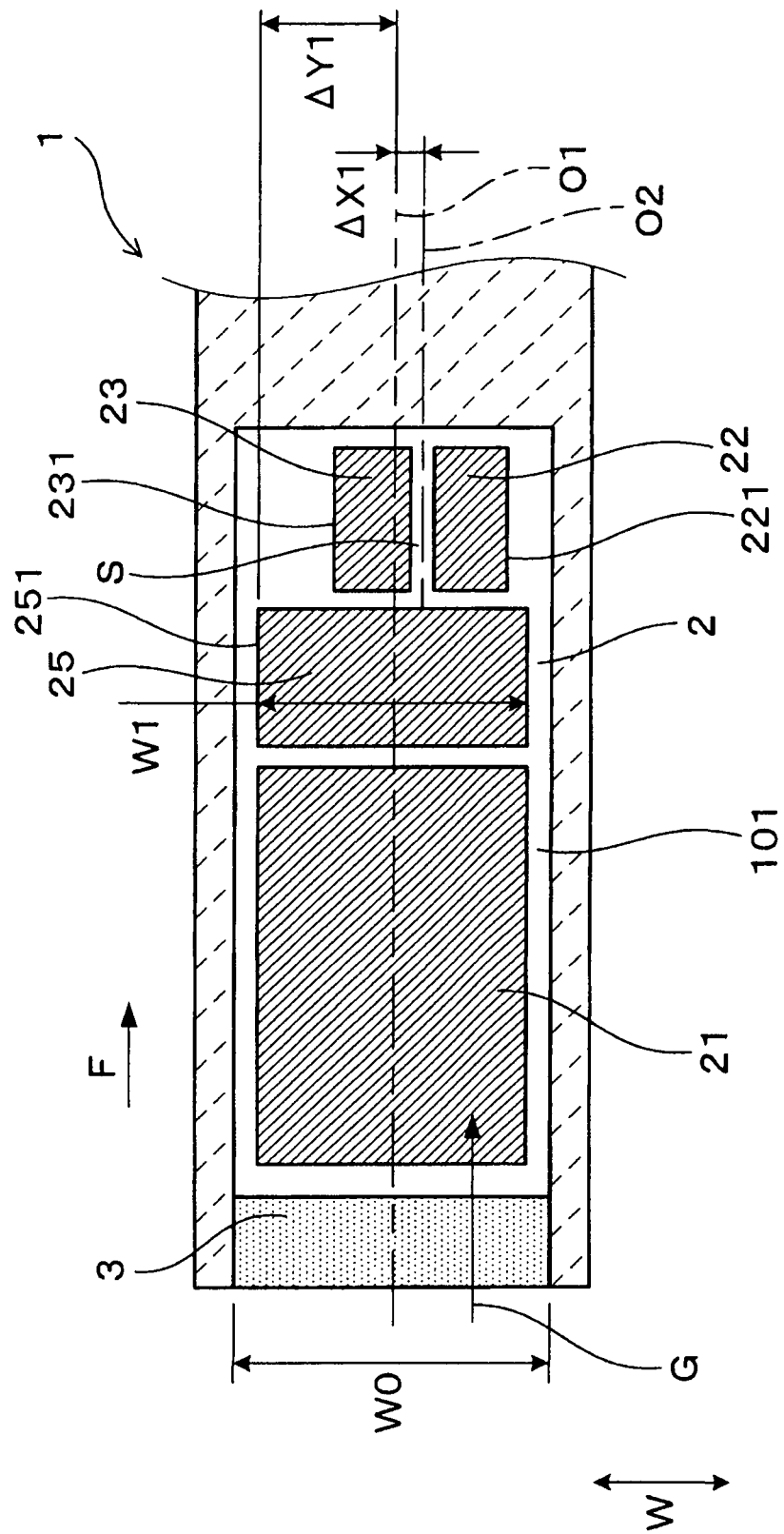
FIG. 14 is a XIV-XIV cross-sectional view of FIG. 13 according to the fourth embodiment.

As illustrated in FIGS. 13 and 14, the fourth embodiment shows the case where the gas sensor 1 has a second pump cell 45 in addition to the configuration in the first embodiment.

The second pump cell 45 has a second pump electrode 25 to be exposed to the gas G on the first main surface 201 on the gas chamber 101 side of the solid electrolyte 2. The second pump electrode 25 is arranged, on the first main surface 201 of the solid electrolyte 2, between the pump electrode 21 and the monitor and sensor electrodes 22 and 23. The pump electrode 21 in the pump cell 41 is a first pump electrode.

The second pump cell 45 is configured to apply a voltage between the second pump electrode 25 and the reference electrode 24 to adjust the oxygen concentration in the gas G in the gas chamber 101. In the gas chamber 101, the oxygen concentration in the gas G is adjusted in two stages by the first pump cell 41 and the second pump cell 45.

In the gas sensor 1 in the present embodiment, the oxygen concentration in the gas G in the gas chamber 101 is firstly adjusted by the pump cell 41 and then adjusted even more precisely by the second pump cell 45. Therefore, the oxygen concentration in the gas G reaching the monitor electrode 22 and the sensor electrode 23 can be controlled more precisely and the detection errors by the gas sensor 1 can be smaller.

In the gas sensor 1 in the present embodiment, the oxygen concentration in the gas G reaching the monitor electrode 22 and the sensor electrode 23 is finally adjusted by the second pump cell 45, and a central position of the second pump electrode 25 in the width direction W is O1. Then, when the second pump electrode 25 has a width W1, the amount of shift ΔX1 of the central position O2 in the width direction W of the gap S between the monitor electrode 22 and the sensor electrode 23 has relationship of ΔX1≤¼ W1. The positions ΔY1 of the side surface 221 of the monitor electrode 22 and of the side surface 231 of the sensor electrode 23 relative to the central position O1 of second pump electrode 25 in the width direction W has relationship of ΔY1≤½ W1.

In other words, the position of the side surface 221 of the monitor electrode 22 is positioned same as the position of a side surface 251 of the second pump electrode 25 or inside from the position of the side surface 251 of the second pump electrode 25. The position of the side surface 231 of the sensor electrode 23 is positioned same as the position of the side surface 251 of the second pump electrode 25 or inside from the position of the side surface 251 of the second pump electrode 25.

In the present embodiment, the gas G after passing through the position of arranging the second pump electrode 25 can contact the monitor electrode 22 and the sensor electrode 23 in a manner as equivalent as possible. Therefore, the amounts of decomposing residual oxygen in the gas G can be as equivalent as possible in the monitor electrode 22 and the sensor electrode 23.

Other configurations and the reference signs in the drawings of the gas sensor 1 in the fourth embodiment are same as those in the first and second embodiments and other actions and effects of the fourth embodiment are same as those in the first and second embodiments.

Fifth Embodiment

Figure 15:
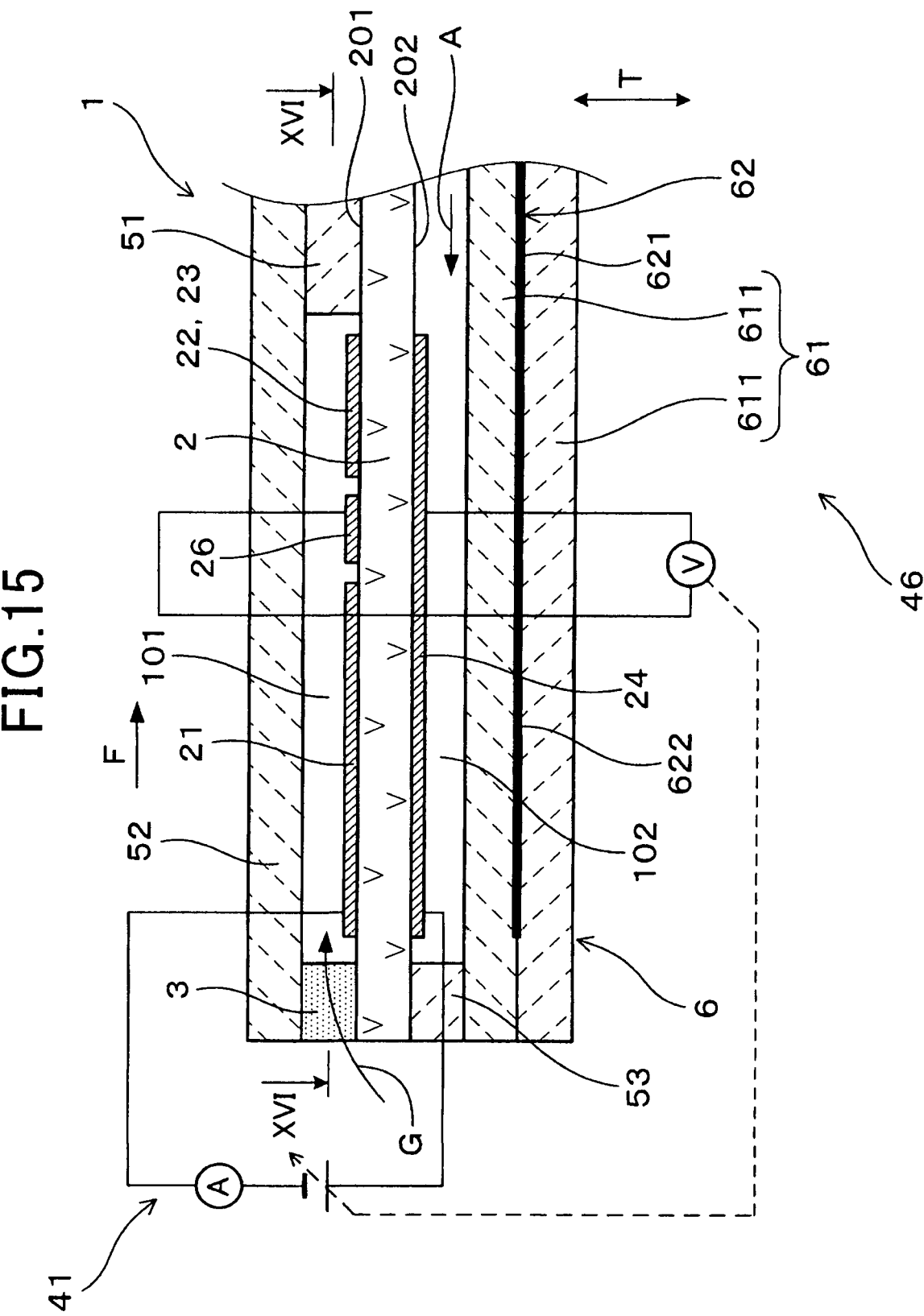
FIG. 15 is a cross-sectional view illustrating a gas sensor according to a fifth embodiment.
Figure 16:
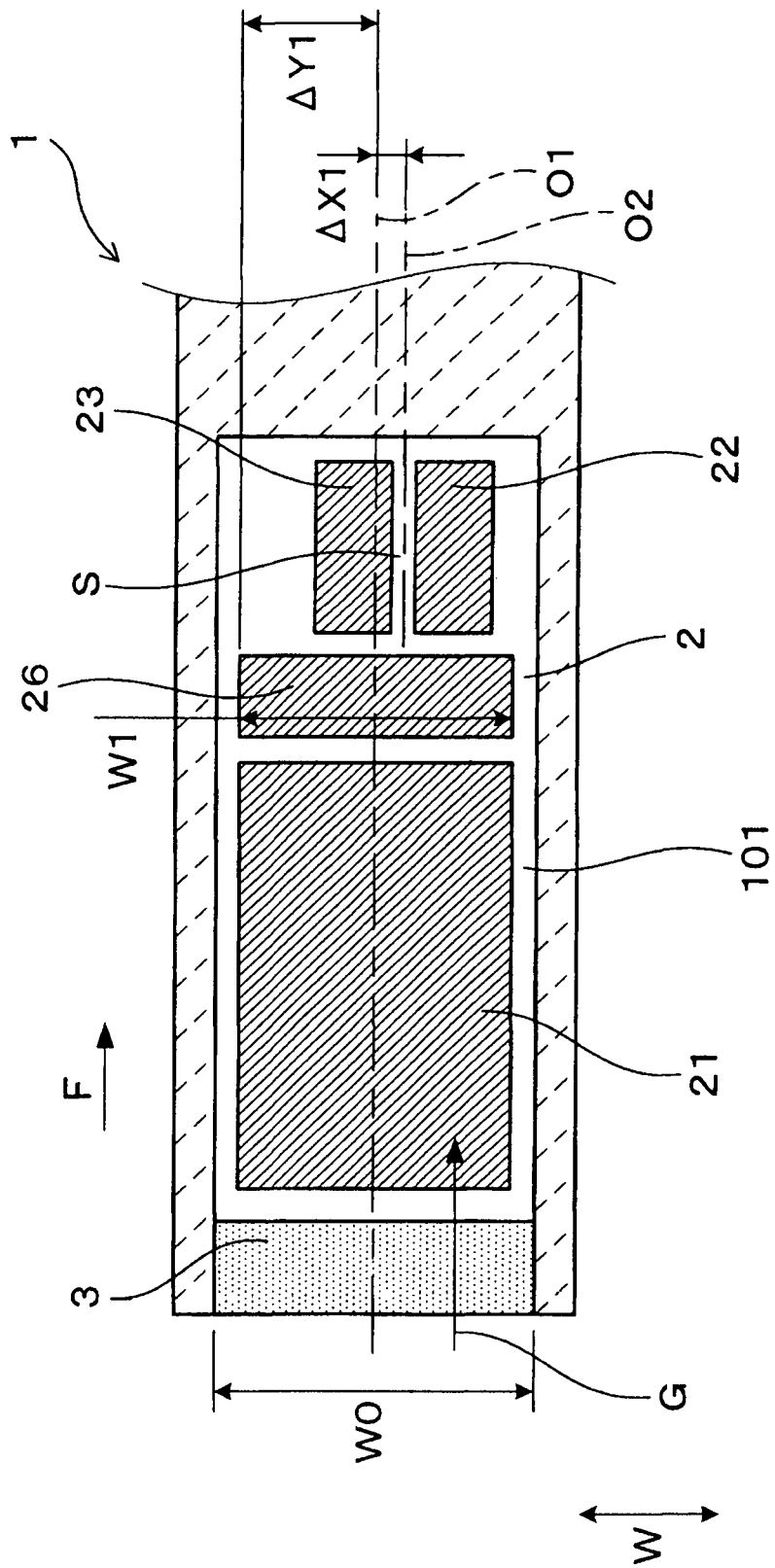
FIG. 16 is a XVI-XVI cross-sectional view of FIG. 15 according to the fifth embodiment.

As illustrated in FIGS. 15 and 16, the fifth embodiment shows the case where the gas sensor 1 has a pump control cell 46 in addition to the configuration in the first embodiment.

The pump control cell 46 has a pump control electrode 26 to be exposed to the gas G on the first main surface 201 on the gas chamber 101 side of the solid electrolyte 2. The pump control electrode 26 is arranged, on the first main surface 201 of the solid electrolyte 2, between the pump electrode 21 and the monitor and sensor electrodes 22 and 23.

The pump control cell 46 is configured to detect the oxygen concentration in the gas G in the gas chamber 101 from an electromotive force developed between the pump control electrode 26 and the reference electrode 24. In the gas sensor 1 in the present embodiment, the oxygen concentration in the gas G in the gas chamber 101 is adjusted by controlling the pump cell 41 to have the electromotive force developed in the pump control cell 46 of a predetermined value. The pump control electrode 26 is arranged, with respect to a direction where the gas G flow, in a position immediately in front of the position where the monitor electrode 22 and the sensor electrode 23 are arranged. Therefore, in the present embodiment, the oxygen concentration in the gas G reaching the monitor electrode 22 and the sensor electrode 23 can be more precisely controlled and the detection errors in the gas sensor 1 can be less.

In the gas sensor 1 in the present embodiment, the oxygen concentration in the gas G reaching the monitor electrode 22 and the sensor electrode 23 is finally adjusted by the pump control cell 46, and the pump control electrode 26 has a central position O1 in the width direction W. Then, when the pump control electrode 26 has a width W1, the amount of shift ΔX1 of the central position O2 in the width direction W of the gap S between the monitor electrode 22 and the sensor electrode 23 has relationship of ΔX1≤¼ W1. The positions ΔY1 of the side surface 221 of the monitor electrode 22 and of the side surface 231 of the sensor electrode 23 relative to the central position O1 in the width direction W of the pump control electrode 26 has relationship of ΔY1≤½ W1.

In the fifth embodiment, the gas G after passing through the position where the pump control electrode 26 is arranged can contact the monitor electrode 22 and the sensor electrode 23 in a manner as equivalent as possible. Therefore, the amounts of decomposing residual oxygen in the gas G can be as equivalent as possible in the monitor electrode 22 and the sensor electrode 23.

Other configurations and the reference signs in the drawings of the gas sensor 1 in the fifth embodiment are same as those in the first and second embodiments and other actions and effects of the present embodiment are same as those in the first and second embodiments.

REFERENCE SIGNS LIST

1 Gas Sensor
101 Gas Chamber
102 Reference Gas Chamber
103 First Gas Chamber
104 Second Gas Chamber
105 Small Space
2 Solid Electrolyte
21 Pump Electrode
22 Monitor Electrode
23 Sensor Electrode
24 Reference Electrode
3 Diffusion resistance
41 Pump Cell
42 Monitor Cell
43 Sensor Cell
6 Heater
61 Insulator
62 Electrical Conductor
622 Heat Generation Portion
G Gas
A Reference Gas
S Gap

The invention claimed is:

1. A gas sensor, measuring concentration of a specific gas component in a gas containing oxygen, comprising:
a plate shaped solid electrolyte having oxygen ion conductivity;
a gas chamber formed on a side of a first main surface of the solid electrolyte to have the gas introduced thereinto through a gas introduction part;
a reference gas chamber formed on a side of a second main surface of the solid electrolyte to have a reference gas introduced thereinto;
a pump electrode provided on the first main surface of the solid electrolyte;
a monitor electrode provided on the first main surface of the solid electrolyte and positioned on a downstream side in a direction of flow of the gas from a position where the pump electrode is provided;
a sensor electrode provided on the first main surface of the solid electrolyte and aligned with the monitor electrode in a direction that is perpendicular to the direction of the flow;
a reference electrode provided on the second main surface of the solid electrolyte; and
a heater arranged facing the solid electrolyte via the gas chamber or the reference gas chamber to heat the solid electrolyte, wherein
part of the pump electrode, the reference electrode, and the solid electrolyte forms a pump cell, the pump cell being configured to apply a voltage between the pump electrode and the reference electrode to adjust oxygen concentration in the gas in the gas chamber,
part of the monitor electrode, the reference electrode, and the solid electrolyte forms a monitor cell to detect the oxygen concentration in the gas chamber on the basis of an oxygen ion current flowing between the monitor electrode and the reference electrode,
part of the sensor electrode, the reference electrode, and the solid electrolyte forms a sensor cell to detect the oxygen concentration and the concentration of the specific gas component in the gas chamber on the basis of an oxygen ion current flowing between the sensor electrode and the reference electrode,
the gas sensor is configured to detect the concentration of the specific gas component by subtracting the oxygen ion current detected by the monitor cell from the oxygen ion current detected by the sensor cell,
the gas chamber has a spatial width constant in a width direction orthogonal to the direction of flow in a position where the pump electrode, the monitor electrode, and the sensor electrode are provided on the solid electrolyte,
a gap exists between the monitor electrode and the sensor electrode in the width direction,
in the width direction, an amount of shift $\Delta X1$ of a central position of the gap between the monitor electrode and the sensor electrode from a central position of the pump electrode has relationship of, where the pump electrode has a width W1, $0<\Delta X1 \leq \frac{1}{4} W1$, and distances $\Delta Y1$ from the central position of the pump electrode to a side surface of the monitor electrode and to a side surface of the sensor electrode have relationship of $0<\Delta Y1 \leq \frac{1}{2} W1$,
the pump electrode, the sensor electrode and the monitor electrode are each disposed in the gas chamber,
the sensor electrode and the monitor electrode are each disposed on the solid electrolyte,
a distance between the sensor electrode and the heater and a distance between the monitor electrode and the heater are the same in a thickness direction of the gas sensor, the thickness direction being orthogonal to the direction of the flow,
a distance between to the sensor electrode and the gas introduction part and a distance between the monitor electrode and the gas introduction part are the same in the direction of the flow of the gas,
the distance $\Delta Y1$ from the central position of the pump electrode to the side surface of the sensor electrode is greater than the amount of shift $\Delta X1$;
the gas chamber is configured by a single chamber in which the pump electrode, the sensor electrode and the monitor electrode are disposed; and
$W0>W2>W1$, where W0 is the spatial width of the gas chamber in the width direction, W1 is the width of the pump electrode in the width direction, and W2 is the width of the heater in the width direction.

2. The gas sensor, according to claim 1, wherein the thickness direction is orthogonal to the width direction and the heater includes a heat generation portion, a distance from a surface of the pump electrode to a surface of the heat generation portion, a distance from a surface of the monitor electrode to a surface of the heat generation portion, and a distance from a surface of the sensor electrode to a surface of the heat generation portion are identical.

3. The gas sensor, according to claim 1, wherein,
in the width direction, a width of the monitor electrode and a width of the sensor electrode are approximately identical, and,
in the direction of flow, a distance from an end face on a downstream side of the pump electrode to an end face on an upstream side of the monitor electrode and a distance from an end face on a downstream side of the pump electrode to an end face on an upstream side of the sensor electrode are approximately identical.

4. The gas sensor, according to claim 1, wherein, in the width direction:
a position of a side surface of the monitor electrode is positioned inside of a position of a first side surface of the pump electrode; and
a position of a side surface of the sensor electrode is positioned inside of a position of a second side surface of the pump electrode, the first and second side surfaces of the pump electrode being positioned on opposite sides of the pump electrode in the width direction.

5. The gas sensor, according to claim 1, wherein:
a distance from the end face on the downstream side of the pump electrode to the end face on the upstream side of the monitor electrode in the direction of the flow and a distance from the end face on the downstream side of the pump electrode to the end face on the upstream side of the sensor electrode in the direction of the flow are the same.

6. A gas sensor, measuring concentration of a specific gas component in a gas containing oxygen, comprising:
a plate shaped solid electrolyte having oxygen ion conductivity;
a gas chamber formed on a side of a first main surface of the solid electrolyte to have the gas introduced thereinto through a gas introduction part;
a reference gas chamber formed on a side of a second main surface of the solid electrolyte to have a reference gas introduced thereinto;
a pump electrode provided on the first main surface of the solid electrolyte;
a monitor electrode provided on the first main surface of the solid electrolyte and positioned on a downstream side in a direction of flow of the gas from a position where the pump electrode is provided;
a sensor electrode provided on the first main surface of the solid electrolyte and aligned with the monitor electrode in a direction that is perpendicular to the direction of the flow;
a reference electrode provided on the second main surface of the solid electrolyte; and
a heater arranged facing the solid electrolyte via the gas chamber or the reference gas chamber to heat the solid electrolyte, wherein
part of the pump electrode, the reference electrode, and the solid electrolyte forms a pump cell, the pump cell being configured to apply a voltage between the pump electrode and the reference electrode to adjust oxygen concentration in the gas in the gas chamber,
part of the monitor electrode, the reference electrode, and the solid electrolyte forms a monitor cell to detect the oxygen concentration in the gas chamber on the basis of an oxygen ion current flowing between the monitor electrode and the reference electrode,
part of the sensor electrode, the reference electrode, and the solid electrolyte forms a sensor cell to detect the oxygen concentration and the concentration of the specific gas component in the gas chamber on the basis of an oxygen ion current flowing between the sensor electrode and the reference electrode,
the gas sensor is configured to detect the concentration of the specific gas component by subtracting the oxygen ion current detected by the monitor cell from the oxygen ion current detected by the sensor cell,
the gas chamber has a spatial width constant in a width direction orthogonal to the direction of flow in a position where the pump electrode, the monitor electrode, and the sensor electrode are provided on the solid electrolyte,
the heater has an insulator and a heat generation portion embedded in the insulator to generate heat by energization, the heat generation portion provided to correspond to a projected position of entire plane region of the solid electrolyte provided with the pump electrode, the monitor electrode, and the sensor electrode,
a gap exists between the monitor electrode and the sensor electrode in the width direction,
in the width direction, an amount of shift $\Delta X2$ of a central position of the gap between the monitor electrode and the sensor electrode from a central position of the heat generation portion has relationship of, where the heat generation portion has entire width W2 in the width direction (W), $0<\Delta X2 \leq \frac{1}{4} W2$, and distances $\Delta Y2$ from the central position of the heat generation portion to a side surface of the monitor electrode and to a side surface of the sensor electrode have relationship of $0<\Delta Y2 \leq \frac{1}{2} W2$,
the pump electrode, the sensor electrode and the monitor electrode are each disposed in the gas chamber,
the sensor electrode and the monitor electrode are each disposed on the solid electrolyte,
a distance between the sensor electrode and the heater and a distance between the monitor electrode and the heater are the same in a thickness direction of the gas sensor, the thickness direction being orthogonal to the direction of the flow,
a distance between to the sensor electrode and the gas introduction part and a distance between the monitor electrode and the gas introduction part are the same in the direction of the flow of the gas, and
the distance $\Delta Y1$ from the central position of the pump electrode to the side surface of the sensor electrode is greater than the amount of shift $\Delta X1$;
the gas chamber is configured by a single chamber in which the pump electrode, the sensor electrode and the monitor electrode are disposed; and
W0>W2>W1, where W0 is the spatial width of the gas chamber in the width direction, W1 is the width of the pump electrode in the width direction, and W2 is the width of heat generation portion in the width direction.

7. The gas sensor, according to claim 6, wherein a width W1 in the width direction of the pump electrode and entire width W2 in the width direction of the heat generation portion have relationship of W1 W2.

8. The gas sensor, according to claim 6, wherein, in the width direction:
a position of the side surface of the monitor electrode is positioned inside of a position of a first side surface of the heater; and
a position of a side surface of the sensor electrode is positioned inside of a position of a second side surface of the heater, the first and second side surfaces of the heater being positioned on opposite sides of the heater in the width direction.

9. The gas sensor, according to claim 6, wherein:
a distance from the end face on the downstream side of the pump electrode to the end face on the upstream side of the monitor electrode in the direction of the flow and a distance from the end face on the downstream side of the pump electrode to the end face on the upstream side of the sensor electrode in the direction of the flow are the same.

* * * * *